United States Patent
Sheng et al.

(10) Patent No.: US 10,954,223 B2
(45) Date of Patent: *Mar. 23, 2021

(54) CANAGLIFLOZIN MONOHYDRATE AND ITS CRYSTALLINE FORMS, PREPARATION METHODS AND USES THEREOF

(71) Applicant: Hangzhou SoliPharma Co., Ltd., Zhejiang (CN)

(72) Inventors: Xiaoxia Sheng, Zhejiang (CN); Xiaohong Sheng, Zhejiang (CN); Kun Zhao, Zhejiang (CN); Xiaoye Song, Zhejiang (CN)

(73) Assignee: Hangzhou SoliPharma Co., Ltd., Hangzhou (CN)

( * ) Notice: Subject to any disclaimer, the term of this patent is extended or adjusted under 35 U.S.C. 154(b) by 0 days.

This patent is subject to a terminal disclaimer.

(21) Appl. No.: 16/242,879

(22) Filed: Jan. 8, 2019

(65) Prior Publication Data

US 2019/0315727 A1 Oct. 17, 2019

Related U.S. Application Data

(63) Continuation of application No. 15/115,440, filed as application No. PCT/CN2014/081656 on Jul. 4, 2014, now Pat. No. 10,174,010.

(30) Foreign Application Priority Data

Mar. 19, 2014 (CN) .......................... 201410106768.7

(51) Int. Cl.

| C07D 409/10 | (2006.01) |
|---|---|
| A61K 31/7042 | (2006.01) |
| A61K 9/00 | (2006.01) |
| A61K 9/10 | (2006.01) |
| A61K 9/16 | (2006.01) |
| A61K 9/20 | (2006.01) |
| A61K 9/28 | (2006.01) |
| A61K 9/48 | (2006.01) |
| A61K 31/381 | (2006.01) |
| A61K 47/12 | (2006.01) |
| A61K 47/14 | (2017.01) |
| A61K 47/36 | (2006.01) |

(52) U.S. Cl.
CPC .......... *C07D 409/10* (2013.01); *A61K 9/0053* (2013.01); *A61K 9/0095* (2013.01); *A61K 9/10* (2013.01); *A61K 9/1623* (2013.01); *A61K 9/2009* (2013.01); *A61K 9/2013* (2013.01); *A61K 9/2018* (2013.01); *A61K 9/2054* (2013.01); *A61K 9/2813* (2013.01); *A61K 9/2853* (2013.01); *A61K 9/4858* (2013.01); *A61K 9/4866* (2013.01); *A61K 31/381* (2013.01); *A61K 31/7042* (2013.01); *A61K 47/12* (2013.01); *A61K 47/14* (2013.01); *A61K 47/36* (2013.01); *C07B 2200/13* (2013.01)

(58) Field of Classification Search
CPC ..................................................... C07D 409/10
See application file for complete search history.

(56) References Cited

U.S. PATENT DOCUMENTS

| 7,943,582 | B2 | 5/2011 | Nomura et al. |
| 7,943,788 | B2 | 5/2011 | Nomura et al. |
| 10,174,010 | B2 * | 1/2019 | Sheng .................. A61K 31/381 |

FOREIGN PATENT DOCUMENTS

| CN | 103554092 A | 2/2014 | |
| CN | 103588762 A | 2/2014 | |
| CN | 103641822 A | 3/2014 | |
| WO | WO-2005012326 A1 | 2/2005 | |
| WO | WO-2008069327 A1 | 6/2008 | |
| WO | WO-2009035969 A1 | 3/2009 | |
| WO | WO-2011142478 A1 | 11/2011 | |
| WO | WO-2012006298 A2 | 1/2012 | |
| WO | WO-2015071761 A2 | 5/2015 | |
| WO | WO-2015139386 A1 | 9/2015 | |
| WO | WO2015181692 * | 12/2015 | .......... C07D 409/10 |
| WO | WO-2015181692 A1 * | 12/2015 | .......... C07D 409/10 |

OTHER PUBLICATIONS

International Search Report and Written Opinion for International Application No. PCT/CN2014/081656, State Intellectual Property Office of the P.R. China, China, dated Dec. 23, 2014, 4 pages.
Office Action dated Feb. 28, 2018, in U.S. Appl. No. 15/115,440, inventor Sheng, Xiaoxia, S., §371(c) filed Aug. 1, 2016, 7 pages.
Office Action dated Oct. 4, 2017, in U.S. Appl. No. 15/115,440, inventor Sheng, Xiaoxia, S., §371(c) filed Aug. 1, 2016, 9 pages.

* cited by examiner

*Primary Examiner* — John S Kenyon
(74) *Attorney, Agent, or Firm* — Sterne, Kessler, Goldstein & Fox P.L.L.C.

(57) ABSTRACT

The present invention relates to canagliflozin Monohydrate and its crystalline forms, which as compared to the prior art, have higher stability in water or aqueous system, are more suitable for wet granulation processes or suspension preparations and have good storage stability; the present invention also relates to preparation methods of canagliflozin Monohydrate and its crystalline forms, pharmaceutical compositions thereof and uses thereof in preparation of drugs for treating diseases such as diabetes, diabetes complications, obesity and so on.

6 Claims, 5 Drawing Sheets

CANAGLIFLOZIN MONOHYDRATE AND ITS CRYSTALLINE FORMS, PREPARATION METHODS AND USES THEREOF

BACKGROUND OF THE INVENTION

Field of the Invention

The present invention relates to the technical field of crystallization in pharmaceutical chemistry. Specifically, the present invention relates to canagliflozin Monohydrate and its crystalline forms, preparation methods, pharmaceutical compositions and uses thereof.

Background

Canagliflozin is a sodium-glucose co-transporter 2 (SGLT2) inhibitor. It can lower blood glucose concentration by blocking reabsorption of glucose in the renal tubular into the bloodstream and increasing urinary glucose excretion. Canagliflozin was developed by Johnson & Johnson's Janssen Pharmaceuticals and approved for marketing by the FDA in March 2013 under the trade name of Invokana. The drug was approved for treatment of type II diabetes in adults, but unsuitable for type I diabetes or diabetic ketoacidosis. Its dosage form is capsule-shaped film-coated tablets. Two strengths are 100 mg and 300 mg, the 100 mg tablet is yellow, the 300 mg tablet is white. The active ingredient is canagliflozin hemihydrate.

The chemical name of Canagliflozin is (1S)-1,5-anhydro-1-[3-[[5-(4-fluorophenyl)-2-thienyl]methyl]-4-methylphenyl]-D-glucitol. Its molecular formula is $C_{24}H_{25}FO_5S$ and molecular weight is 444.52. The chemical structural formula of Canagliflozin is shown below:

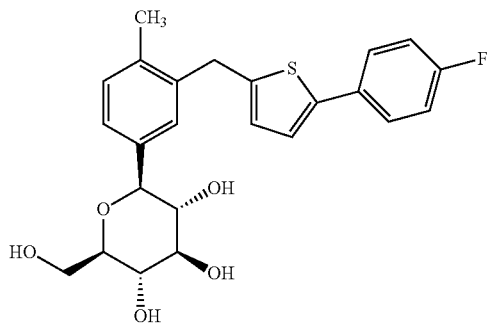 [SMILES: Cc1ccc([C@@H]2O[C@H](CO)[C@@H](O)[C@H](O)[C@H]2O)cc1Cc1ccc(-c2ccc(F)cc2)s1]

Patent documents WO2005/012326A1 and U.S. Pat. No. 7,943,788B2 disclosed canagliflozin and preparation methods thereof. For convenience, the canagliflozin prepared according to U.S. Pat. No. 7,943,788B2 is referred to as the known canagliflozin in the present application.

Patent documents WO2008/069327A1 and U.S. Pat. No. 7,943,582B2 disclosed a crystalline form of canagliflozin hemihydrate and its preparation methods, and characterized it by XRPD and FTIR. For convenience, it is referred to as canagliflozin hemihydrate Form hH1 in the present application.

Patent document CN201310496416.2 disclosed another crystalline form of canagliflozin hemihydrate and its preparation methods, and characterized it by XRPD, IR, DSC and TGA. For convenience, it is referred to as canagliflozin hemihydrate Form hH2 in the present application.

Patent document WO2009/035969A1 disclosed a crystalline form of canagliflozin and its preparation methods, and characterized it by XRPD. For convenience, it is referred to as canagliflozin Form A in the present application.

Patent document CN201310556655.2 disclosed canagliflozin crystalline Form B and its preparation methods, and characterized it by XRPD and DSC. For convenience, it is referred to as canagliflozin Form B in the present application.

Patent document CN201310617597.X disclosed canagliflozin Form C and Form D and their preparation methods. Form C was characterized by XRPD, DSC and TGA, and Form D was characterized by XRPD.

Patent document WO2011/142478A1 disclosed tablets containing canagliflozinb hemihydrate Form hH1. WO2012/006298A2 disclosed bilayer tablets containing canagliflozin hemihydrate as well as their preparation methods.

The present inventors repeated the prior art processes for making the known canagliflozin and canagliflozin Form A, Form B, Form C and Form D, canagliflozin hemihydrate Form hH1 and canagliflozin hemihydrate Form hH2 disclosed in the above documents and tested their properties. The results indicated that the known canagliflozin and canagliflozin Form A were not stable in water, as they failed to maintain their original crystalline forms in the competitive stability test in water and both changed forms; Cangaliflozin Form B, Form C and Form D have poor phase stability and are difficult to be reproduced; canagliflozin hemihydrate Form hH1 has poor phase stability, as it did not maintain its original crystalline form in the competitive stability test in water and changed its form; canagliflozin hemihydrate Form hH2 has poor phase stability and is difficult to be reproduced. The above properties may lead to problems in their pharmaceutical formulations, including variations in active substance content, poor reproducibility, impurities increasing during storage, efficacy decreasing, and so on. Moreover, the known canagliflozin is amorphous. It is well known to those skilled in the art that amorphous forms are less stable, more hygroscopic and unsuitable for applications in solid formulations.

In order to meet the strict requirements for active substances in pharmaceutical formulations and provide more polymorph form options in formulation development, there still is a need to develop novel crystalline forms of canagliflozin.

BRIEF SUMMARY OF THE INVENTION

In view of the defects in the prior art, the objective of the present invention is to provide canagliflozin Monohydrate and its crystalline forms with improved stability and formulation processability. Moreover, the present invention also relates to preparation methods of canagliflozin Monohydrate and its crystalline forms, pharmaceutical compositions and uses thereof.

According to the objective of the present invention, the present invention provides canagliflozin monohydrate (referred to as Monohydrate in the present invention). The structural formula is shown below:

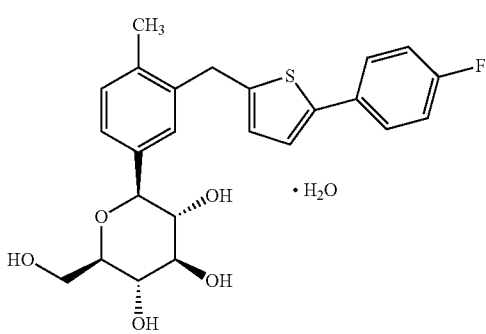 [SMILES: Cc1ccc([C@@H]2O[C@H](CO)[C@@H](O)[C@H](O)[C@H]2O)cc1Cc1ccc(-c2ccc(F)cc2)s1 ; "· H2O"]

The ¹H-NMR data of the Monohydrate is as follows:

¹H-NMR (CD$_3$OD) 2.32 (s, 3H), 3.35-3.53 (m, 4H), 3.71 (d, 1H, J=11.9 Hz), 3.90 (d, 1H, J=11.9 Hz), 4.13 (d, 1H, J=9.3 Hz), 4.17 (s, 2H), 4.9 (s, 4H), 6.70 (d, 1H, J=3.7 Hz), 7.04-7.14 (m, 3H), 7.18 (d, 1H, J=7.8 Hz), 7.26 (d, 1H, J=7.8 Hz), 7.33 (s, 1H), 7.52-7.60 (m, 2H).

The TGA thermogram of the Monohydrate shows that a weight loss of 4.1% occurs before 100° C., which roughly equals the theoretical weight loss of one molecule of water in the Monohydrate.

A preparation method of the Monohydrate is as follows: mixing canagliflozin with an aqueous system, stirring, filtering, drying and obtaining the Monohydrate.

The present invention provides the novel canagliflozin Monohydrate to overcome defects of those known polymorph forms in the prior art. Compared to the known canagliflozin, known canagliflozin crystalline forms and known canagliflozin hemihydrate forms, canagliflozin Monohydrate of the present invention has one or more advantageous properties, such as higher solubility and dissolution rate, better crystal morphology, less tendency for phase transformation and/or dehydration, good thermodynamic stability, good storage stability, low hygroscopicity, better flowability, better compressibility and bulk density, better processing properties, low-levels of residual solvents, etc.

According to the objective of the present invention, the present invention provides canagliflozin monohydrate Form HI (referred to as "Monohydrate Form HI" in the present invention). The structural formula is shown below:

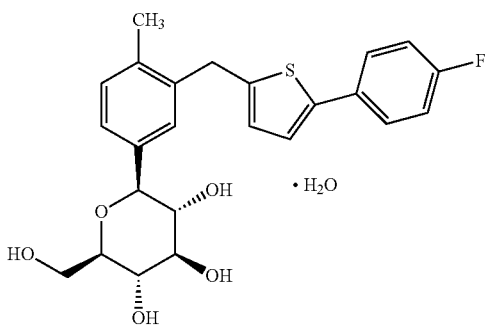 [SMILES: Cc1ccc([C@@H]2O[C@H](CO)[C@@H](O)[C@H](O)[C@H]2O)cc1Cc1ccc(-c2ccc(F)cc2)s1 ; "· H2O"]

Measured using Cu-Kα radiation, the X-ray powder diffraction pattern of Monohydrate Form HI, expressed as 2θ angles, has the following characteristic peaks: 4.3±0.2°, 8.5±0.2°, 12.7±0.2°, 15.4±0.2°, 16.9±0.2°, 19.1±0.2° and 23.0±0.2°.

In a preferable embodiment of the present invention, the X-ray powder diffraction pattern of Monohydrate Form HI, expressed as 2θ angles, has the following characteristic peaks: 4.3±0.2°, 8.5±0.2°, 12.2±0.2°, 12.7±0.2°, 15.4±0.2°, 16.9±0.2°, 18.1±0.2°, 19.1±0.2°, 20.5±0.2°, 23.0±0.2°, 27.0±0.2° and 34.1±0.2°.

In a further preferable embodiment of the present invention, the X-ray powder diffraction pattern of Monohydrate Form HI, expressed as 2θ angles, has the following characteristic peaks and relative intensities:

| 2θ | Relative intensity % |
|---|---|
| 4.3 ± 0.2° | 14.1 |
| 8.5 ± 0.2° | 100.0 |
| 12.2 ± 0.2° | 5.8 |
| 12.7 ± 0.2° | 44.7 |
| 15.4 ± 0.2° | 14.6 |
| 16.9 ± 0.2° | 53.6 |
| 18.1 ± 0.2° | 7.3 |
| 19.1 ± 0.2° | 9.1 |
| 20.5 ± 0.2° | 5.0 |
| 23.0 ± 0.2° | 70.8 |
| 27.0 ± 0.2° | 13.6 |
| 34.1 ± 0.2° | 22.8 |

Non-restrictively, in one embodiment, the X-ray powder diffraction pattern of Monohydrate Form HI is shown in FIG. 5.

The TGA thermogram of Monohydrate Form HI indicates that a weight loss of 4.1% occurs before 100° C., which roughly equals to the theoretical weight loss of one molecule of water in one molecule of Monohydrate Form HI.

The canagliflozin Monohydrate Form HI of the present invention is prepared by any one of the following preparation methods:

(1) Forming a suspension system of canagliflozin in water or in a mixed solvent consisting of water and an organic solvent, wherein the organic solvent is selected from the group consisting of C$_1$ to C$_8$ alcohols, C$_3$ to C$_8$ ketones, C$_3$ to C$_8$ esters, C$_3$ to C$_8$ ethers, C$_5$ to C$_8$ alkanes, C$_1$ to C$_8$ substituted alkanes, C$_6$ to C$_{12}$ aromatics, acetonitrile and the mixtures thereof, stirring or grinding the obtained suspension system for crystallization, and obtaining canagliflozin Monohydrate Form HI.

The C$_1$ to C$_8$ alcohols include but are not limited to methanol, ethanol, isopropanol, butanol and pentanol; the C$_3$ to C$_8$ ketones include but are not limited to acetone, butanone and 4-methyl-2-pentanone; the C$_3$ to C$_8$ esters include but are not limited to ethyl acetate, butyl acetate and isopropyl acetate; the C$_3$ to C$_8$ ethers include but are not limited to methyl tert-butyl ether, 1,4-dioxane, tetrahydrofuran and isopropyl ether; the C$_5$ to C$_8$ alkanes include but are not limited methyl cyclohexane, cyclohexane, n-heptane, n-hexane and petroleum ether; the C$_1$ to C$_8$ substituted alkanes include but are not limited to dichloromethane, chloroform and nitromethane; the C$_6$ to C$_{12}$ aromatics include but are not limited toluene and dimethylbenzene.

Preferably, the organic solvent is selected from the group consisting of ethanol, isopropanol, butanol, acetone, butanone, ethyl acetate, methyl tert-butyl ether, petroleum ether, 1,4-dioxane, tetrahydrofuran, acetonitrile, methyl cyclohexane, cyclohexane, n-heptane and toluene.

The volume ratio of water to the organic solvent in the mixed solvent may be arbitrary; and the obtained mixed solvent consisting of water and the organic solvent can be either homogeneous or heterogeneous.

Preferably, the amount of canagliflozin in the suspension is 1.1 to 1000 times of its solubility in water or in the mixed solvent consisting of water and the organic solvent, more preferably 2 to 300 times.

Preferably, the mass ratio of canagliflozin to water in the suspension system is not more than 24:1.

Preferably, crystal seeds of canagliflozin Monohydrate Form HI are added to the suspension system, the amount of the crystal seeds is from 0.5% to 20% of canagliflozin by weight, more preferably 1% to 5% by weight.

Preferably, the stirring time is from 2 hours to 7 days, more preferably 6 hours to 2 days.

Preferably, the grinding time is from 10 minutes to 8 hours, more preferably 0.5 hours to 3 hours.

Preferably, the operation temperature of the preparation method (1) is 5° C. to 110° C., more preferably 15° C. to 50° C.

Slurrying and grinding for crystallization are used in the preparation method (1). The detailed operation of slurrying is, for example: placing the suspension of canagliflozin into a reaction bottle and stirring for crystallization at the operation temperature. The detailed operation of grinding is, for example: placing the suspension containing canagliflozin in a mortar and grinding for crystallization.

(2) Preparing a solution of canagliflozin in a soluble solvent, mixing the solution of canagliflozin with a slightly soluble solvent or an insoluble solvent of canagliflozin to form a mixed system, meanwhile adding crystal seeds of canagliflozin Monohydrate Form HI, stirring for crystallization and obtaining canagliflozin Monohydrate Form HI.

Preferably, the soluble solvent is selected from the group consisting of methanol, ethanol, butanol, acetone, butanone, ethyl acetate, methyl tert-butyl ether, ethyl ether, dichloromethane, 1,4-dioxane, tetrahydrofuran, acetonitrile, and a mixed solvent consisting of water and a misciable solvent selected from the above solvents, wherein the volume ratio of water to the solvent is not more than 3:1.

Preferably, the concentration of the said solution of canagliflozin is 0.1 to 1 times of its solubility in the soluble solvent, more preferably 0.5 to 1 times.

Preferably, the slightly soluble solvent or the insoluble solvent of canagliflozin is selected from the group consisting of water, isopropyl ether, nitromethane, cyclohexane, n-heptane and toluene.

Preferably, the volume ratio of the soluble solvent to the slightly soluble solvent or the insoluble solvent is 1:3 to 1:50, more preferably 1:5 to 1:15.

Preferably, the mass ratio of canagliflozin to water in the mixed system is no more than 24:1.

Preferably, the solution of canagliflozin and the slightly soluble solvent or the insoluble solvent are mixed by the following methods: i) adding the solution of canagliflozin into the slightly soluble solvent or the insoluble solvent; or ii) adding the slightly soluble solvent or the insoluble solvent into the solution of canagliflozin; or iii) adding the solution of canagliflozin and the slightly soluble solvent or the insoluble solvent into the reaction container simultaneously.

Preferably, the amount of the crystal seeds of canagliflozin Monohydrate Form HI is 0.5% to 20% of canagliflozin by weight, more preferably 1% to 5% by weight.

Preferably, the stirring time is from 5 minutes to 24 hours, more preferably 0.5 hours to 5 hours.

Preferably, the operation temperature of the preparation method (2) is from 5° C. to 80° C., more preferably 15° C. to 45° C.

Anti-solvent for crystallization is used in the preparation method (2). The detailed operation is, for example: mixing a solution of canagliflozin with a slightly soluble solvent or an insoluble solvent of canagliflozin, adding the crystal seeds of canagliflozin Monohydrate Form HI simultaneously, then stirring for crystallization.

(3) Forming a saturated solution of canagliflozin in a soluble solvent, adding crystal seeds of canagliflozin Monohydrate Form HI into the saturated solution, cooling and stirring for crystallization, and obtaining canagliflozin Monohydrate Form HI.

Preferably, the soluble solvent is a miscible solvent mixture consisting of water and a organic solvent, wherein the organic solvent is selected from the group consisting of methanol, ethanol, butanol, acetone, butanone, ethyl acetate, methyl tert-butyl ether, ethyl ether, or dichloromethane, 1,4-dioxane, tetrahydrofuran and acetonitrile, and the volume ratio of water to the organic solvent in the misciable solvent mixture is not more than 3:1.

Preferably, the mass ratio of canagliflozin to water in the saturated solution of canagliflozin is not more than 24:1.

Preferably, the initial temperature of the saturated solution of canagliflozin is from 30° C. to 80° C., more preferably 30° C. to 50° C.

Preferably, the amount of the crystal seeds of canagliflozin Monohydrate Form HI is from 0.5% to 20% of canagliflozin by weight, more preferably 1% to 5% by weight.

Preferably, the saturated solution of canagliflozin is cooled to −15° C. to 30° C., more preferably 5° C. to 15° C.

Preferably, the stirring time for crystallization is from 5 minutes to 24 hours, more preferably 0.5 hours to 5 hours.

Cooling for crystallization is used in the preparation method (3). The detailed operation is, for example: forming a saturated solution of canagliflozin (e.g., adding canagliflozin to a soluble solvent, heating to dissolve completely, then cooling to obtain the saturated solution of canagliflozin at the appropriate temperature), adding the crystal seeds of canagliflozin Monohydrate Form HI into the saturated solution, cooling, and stirring for crystallization.

In the above preparation methods (1) to (3) of canagliflozin Monohydrate Form HI, the crystal seeds of canagliflozin Monohydrate Form HI are prepared by methods, such as mixing canagliflozin with a mixed solvent consisting of water, isopropanol and cyclohexane to form a suspension, stirring for crystallization, filtering, drying, and obtaining the crystal seeds of canagliflozin Monohydrate Form HI.

In the above preparation methods (1) to (3) of canagliflozin Monohydrate Form HI, the "stirring" was performed by routine techniques in the field, for example, magnetic stirring or mechanical stirring. The stirring speed is from 50 to 1800 r/min, preferably 300 to 900 r/min.

In the above preparation methods (1) to (3) of canagliflozin Monohydrate Form HI, filtering and drying of the obtained canagliflozin Monohydrate Form HI were performed using routine techniques in the field. The "filtering" usually refers to suction filtration at room temperature at a pressure less than the atmospheric pressure, preferably less than 0.09 MPa. The "drying" in general refers to dry at 20° C. to 50° C. at a pressure which is not more than the atmospheric pressure, preferably less than 0.09 MPa; the drying time is usually from 0.5 hours to 48 hours.

Canagliflozin Monohydrate Form HI of the present invention has the following advantageous properties:

① At room temperature, the competitive stability test was performed by mixing canagliflozin Monohydrate Form HI of the present invention, the known canagliflozin, canagliflozin hemihydrate Form hH1 and canagliflozin Form A with water. The result showed that the known canagliflozin, canagliflozin hemihydrate Form hH1 and canagliflozin Form A all failed to maintain their original crystalline forms and transformed to canagliflozin Monohydrate Form HI of the present invention. In contrast, canagliflozin Monohydrate Form HI of the present invention maintained its original crystalline form in the test, which indicates that canagliflozin Monohydrate Form HI of the present invention has better stability in water or an aqueous system.

② When placed in a desiccator at room temperature and 10% to 90% RH for 4 months, the crystalline form of canagliflozin Monohydrate Form HI of the present invention remained unchanged.

The above advantageous properties indicate that compared to the known canagliflozin, known canagliflozin hemihydrate Form hH1 and known canagliflozin Form A, the canagliflozin Monohydrate Form HI of the present invention has better stability in water or an aqueous system, is more suitable for wet granulation processes of making solid formulations or suspensions, and has better storage stability. It is more humidity robust and thus less likely to have content uniformity and stability issues induced by the environment during pharmaceutical production and storage, and thus reducing the risk of inefficacy and safety caused thereby, and improving dosing accuracy.

According to the objective of the present invention, the present invention also provides canagliflozin Monohydrate Form HII (referred to as "Monohydrate Form HII" in the present invention). The structural formula is shown below:

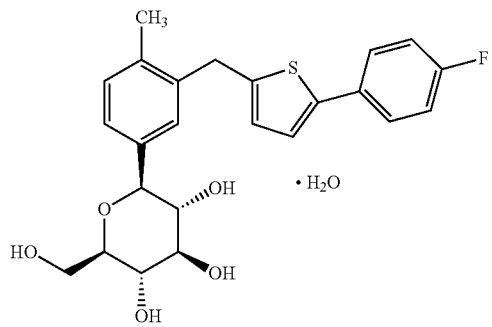 [SMILES: Cc1ccc([C@@H]2O[C@H](CO)[C@@H](O)[C@H](O)[C@H]2O)cc1Cc1ccc(-c2ccc(F)cc2)s1 ; "· H2O"]

Measured using Cu-Kα radiation, the X-ray powder diffraction pattern of the Monohydrate Form HII, expressed as 2θ angles, has the following characteristic peaks: 3.9±0.2°, 6.6±0.2°, 9.9±0.2°, 13.3±0.2°, 19.5±0.2°, 22.9±0.2° and 28.0±0.2°.

In a preferable embodiment of the present invention, the X-ray powder diffraction pattern of the Monohydrate Form HII, expressed as 2θ angles, has the following characteristic peaks with their relative intensities:

| 2θ | Relative intensity % |
|---|---|
| 3.9 ± 0.2° | 10.8 |
| 6.6 ± 0.2° | 54.2 |
| 9.9 ± 0.2° | 17.7 |
| 13.3 ± 0.2° | 11.4 |
| 19.5 ± 0.2° | 100 |
| 22.9 ± 0.2° | 29.5 |
| 28.0 ± 0.2° | 20.8 |

In a further preferable embodiment of the present invention, the X-ray powder diffraction pattern of the Monohydrate Form HII is shown in FIG. 7.

The Fourier transform infrared spectrum of the Monohydrate Form HII shows characteristic peaks at the wave numbers of 3372, 2914, 1509, 1438, 1233, 1161, 1086, 1054, 1022, 953, 889, 831, 799 and 613 $cm^{-1}$.

A preparation method of the Monohydrate Form HII is either of the following:

(1) Forming a solution of canagliflozin in a mixed solvent consisting of water and an organic solvent, wherein the organic solvent is selected from the group consisting of $C_1$ to $C_4$ alcohols, $C_3$ to $C_4$ ketones, 1,4-dioxane, acetonitrile, and their mixtures, adding crystal seeds of canagliflozin Monohydrate Form HII or a polymer compound selected from the group consisting of polyethylene glycol, polyvinylpyrrolidone, Carbomer, ethyl cellulose, sodium carboxymethyl cellulose, hydroxypropylcellulose, Poloxamer, polymethylmethacrylate and hydroxypropylmethylcellulose, forming a solution system or a suspension system, volatilizing the solution system or the suspension system under atmospheric conditions for crystallization, filtering, washing the crystals, drying, and obtaining the Monohydrate Form HII.

The $C_1$ to $C_4$ alcohols are methanol, ethanol, n-propanol, isopropanol, butanol or 2-butanol; The $C_3$ to $C_4$ ketones are acetone or butanone.

Preferably, the organic solvent is isopropanol, acetone, or acetonitrile.

Preferably, the volume ratio of water to the organic solvent in the mixed solvent is from 4:1 to 1:4, more preferably from 1:1 to 1:3.

Preferably, the concentration of the solution of canagliflozin is 0.2 to 1 times of its solubility in the mixed solvent consisting of water and the organic solvent, more preferably 0.5 to 1 times.

Preferably, the molecular weight of polyethylene glycol is from 200 to 8,000; preferably, the molecular weight of polyvinylpyrrolidone is from 5,000 to 7,000; preferably, the molecular weight of Carbomer is from 1,000,000 to 4,000,000; preferably, the content of ethoxyl in ethyl cellulose is from 44% to 51%; preferably, the molecular weight of sodium carboxymethyl cellulose is from 90,000 to 700,000; preferably, the molecular weight of hydroxypropyl cellulose is from 50,000 to 1,250,000; preferably, the molecular weight of Poloxamer is from 1,000 to 16,000; preferably, the molecular weight of polymethylmethacrylate is from 300,000 to 450,000; preferably, the molecular weight of hydroxypropylmethylcellulose is from 10,000 to 1,500,000.

Preferably, the polymer compound is selected from the group consisting of hydroxypropyl cellulose, hydroxypropylmethylcellulose and polyethylene glycol.

Preferably, the amount of the polymer compound is 2% to 10% of canagliflozin by weight, more preferably 2% to 5% by weight. The polymer compound may be added in the form of solid or solution or suspension. When the polymer compound is added in the form of solution or suspension, the solvent of the solution or the suspension is water or is the same as the mixed solvent consisting of water and the organic solvent that is used for preparing the solution of canagliflozin. When the polymer compound is added in the form of suspension, the volume of the solvent used in the suspension is 0.04 to 0.2 times of the volume of mixed solvent in the solution of canagliflozin, more preferably 0.1 to 0.2 times. When the polymer compound is added in the form of solution, the concentration of the solution is 0.2 to 1 times of its solubility in the solvent, more preferably 0.5 to 1 times.

Preferably, the mass ratio of canagliflozin to water in the solution system or the suspension system is not more than 24:1.

Preferably, the amount of the crystal seeds of canagliflozin Monohydrate Form HII is 2 wt % to 10 wt % of canagliflozin in canagliflozin solution, more preferably 5% to 10 wt %.

Preferably, the temperature of the solution of canagliflozin formed in the mixed solvent consisting of water and the organic solvent is 10 to 60° C., more preferably 20 to 40° C.

Preferably, volatilizing under atmospheric conditions for crystallization lasts 1 to 5 days, more preferably 1 to 3 days.

Preferably, the washing solvent is selected from the group consisting of water, ethanol, ethyl acetate, tetrahydrofuran and mixtures thereof; the volume of the washing solvent is 0.3 to 1 times of the volume of the solvent used in preparing the Monohydrate Form HII, more preferably 0.8 to 1 times.

Preferably, the drying temperature is 10 to 40° C., more preferably 20 to 30° C.

Preferably, the drying time is 10 to 48 hours, more preferably 10 to 24 hours.

The preparation method of the crystal seeds of canagliflozin Monohydrate Form HII, for example, is: mixing canagliflozin with a mixed solvent consisting of water and acetonitrile (the volume ratio of water to acetonitrile is 1:2) to form a clear solution, adding hydroxypropyl cellulose, forming a solution system, volatilizing under atmospheric conditions for crystallization, filtering, drying, and obtaining the crystal seeds of canagliflozin Monohydrate Form HII.

The solution system or the suspension system is formed under stirring. The "stirring" was performed by routine techniques in the field, for example magnetic stirring or mechanical stirring, The stirring speed is 50 to 1800 r/min, preferably 300 to 900 r/min.

The "filtering" was performed by routine techniques in the field. It usually refers to suction filtration at room temperature under a pressure less than the atmospheric pressure, preferably less than 0.09 MPa.

Polymer compounds as template and volatilizing under atmospheric conditions for crystallization are used in the above preparation method (1). The detailed operation, for example, is: placing the clear solution of canagliflozin in an opened glass vial, adding a polymer compound, volatilizing under atmospheric conditions for crystallization with the glass vial uncovered or covered by a lid with holes, filtering, obtaining a mixture of the Monohydrate Form HII and the polymer compound, then adding a washing solvent to it and stirring for a period of time to remove the polymer compound, drying, and obtaining the Monohydrate Form HII.

(2) Placing canagliflozin in an environment at room temperature with the relative humidity in the range of 57% to 75% for 1 to 3 days, and obtaining the Monohydrate Form HII.

Environmental humidities are utilized in the preparation method (2) for crystallization. The detailed operation, for example, is: placing canagliflozin at room temperature with the relative humidity in the range of 57% to 75% for a period of time, such as, in a desiccator or a humidity chamber, and obtaining the Monohydrate Form HII.

The canagliflozin Monohydrate Form HII in the present invention has the following advantageous properties:

① At room temperature, the competitive stability test was performed by mixing canagliflozin Monohydrate Form HII of the present invention, the known canagliflozin, known canagliflozin hemihydrate Form hH1 and known canagliflozin Form A with water. The result showed that the known canagliflozin, canagliflozin hemihydrate Form hH1 and canagliflozin Form A all failed to maintain their original crystalline forms and transformed to canagliflozin Monohydrate Form HII of the present invention, while canagliflozin Monohydrate Form HII of the present invention maintained its original crystalline form in the test, indicating that canagliflozin Monohydrate Form HII in the present invention has better stability in water or aqueous system.

② When stored in desiccators at room temperature with relative humidities from 57% to 75% for 1 day, the known canagliflozin transformed to canagliflozin Monohydrate Form HII of the present invention; continuing stored for 4 months, the crystalline form of the canagliflozin Monohydrate Form HII remained unchanged.

The above advantageous properties indicate that, compared to the known canagliflozin, known canagliflozin hemihydrate Form hH1 and known canagliflozin Form A, canagliflozin Monohydrate Form HII of the present invention has better stability in water or an aqueous system and is more suitable for wet granulation processes of making solid formulations or suspensions, and has better storage stability at room temperature with varying humidity. It is more humidity robust and thus less likely to have content uniformity and stability issues induced by environment during pharmaceutical production and storage, thus reduce the risk of inefficacy and safety caused thereby and improve dosing accuracy.

In the preparation methods of the Monohydrate Form HI and the Monohydrate Form HII of the present invention, canagliflozin starting material may be the known canagliflozin compound or any crystalline forms thereof, canagliflozin hemihydrate or any crystalline forms thereof or canagliflozin amorphous form as disclosed in patent documents (such as WO2005/012326A1 and U.S. Pat. No. 7,943,788B2, WO2008/069327A1 and U.S. Pat. No. 7,943,582B2, CN201310496416.2, WO2009/035969A1, CN201310-556655.2, CN201310617597.X). Those patent documents are hereby incorporated by reference in their entireties.

In the present invention, "crystal" or "crystalline form" refers to that characterized by X-ray powder diffraction pattern. Those skilled in the art are capable of understanding that the experimental error depends on instrumental conditions, sample preparation and sample purity. In particular, it is well known to those skilled in the art that X-ray diffraction patterns may change with the changes of instrumental conditions. It needs to be particularly pointed out that the relative intensities of X-ray diffraction peaks may also change with the changes of experimental conditions, so the order of peak intensities should not be considered as the only or conclusive factor. Additionally, experimental errors in the angles of diffraction peaks are usually 5% or less, these errors should also be considered, and usually differences within ±0.2° are allowed. Additionally, experimental factors such as sample height may lead to overall peak shifts, and usually a certain shift is allowed. Therefore, those skilled in the art are capable of understanding that any crystalline forms having the same or similar characteristic peaks as those of the present invention are within the scope of the present invention.

Crystalline forms of the present invention are pure and basically free of any other crystalline forms. In the present invention, when "basically free of" is used for describing a novel crystalline form, it means that the content of other crystalline forms in the novel crystalline form is less than 20% (w/w), specifically less than 10% (w/w), more specifically less than 5% (w/w), and further more specifically less than 1% (w/w).

According to the objective of the present invention, the present invention provides a pharmaceutical composition, which comprises a therapeutically and/or preventively effective amount of one or more canagliflozin crystalline forms selected from the group consisting of canagliflozin Monohydrate, canagliflozin Monohydrate Form HI and canagliflozin Monohydrate Form HII of the present invention, and at least one pharmaceutically acceptable excipient or carrier. The pharmaceutical composition may also comprise other crystalline or amorphous forms of canagliflozin and their pharmaceutical acceptable salts. Optionally, the pharmaceutical composition may comprise one or more other active pharmaceutical ingredient(s), which include but are not limited to other antidiabetic agents, anti-hyperglycemic agents, anti-obesity agents, antihypertensive agents, anti-platelet agents, anti-atherosclerotic agents, hypolipidemic agents, and so on.

The pharmaceutical composition may be made into certain drug dosage forms for oral administration or parenteral administration. Suitable dosage forms for oral administration are solid oral formulations including tablets, capsules, granules, pulvis, pills, powders, etc. or liquid oral formulations including solutions, syrups, suspensions, emulsions, etc. In the suspensions, canagliflozin Monohydrate, canagliflozin Monohydrate Form HI or canagliflozin Monohydrate Form HII of the present invention maintains their original solid forms. Examples of suitable dosage forms for parenteral administration are intravenous infusion formulations, intramuscular or subcutaneous formulations, suppositories for rectal administration, inhalation formulations for intranasal administration, or transdermal patches for topical administration. The formulations may be made into suitable dosage forms for rapid release, delayed release or controlled release of the active ingredients.

The pharmaceutically acceptable carriers in the pharmaceutical compositions may be in various forms. In the case of solid oral administration, suitable carriers include but are not limited to: diluents, e.g., starch, corn starch, modified starch, lactose, powdered cellulose, microcrystalline cellulose, anhydrous calcium hydrogen phosphate, tricalcium phosphate, mannitol, sorbitol, and sugar, etc.; adhesives, e.g., Arabia gum, guar gum, gelatin, polyvinylpyrrolidone, hydroxypropyl cellulose, hydroxypropyl methylcellulose, polyethylene glycol, copolyvidone, etc.; disintegrants, e.g., starch, sodium carboxymethyl starch, sodium starch glycolate, pregelatinized starch, crospovidone, cross-linked sodium carboxymethylcellulose, and colloidal silica dioxide, etc.; lubricants, e.g., stearic acid, magnesium stearate, zinc stearate, sodium benzoate, sodium acetate, sodium stearyl fumarate, etc.; glidants, e.g., talc powder, colloidal silica dioxide, etc., complex forming agents, e.g. cyclodextrin and resins of various grades; release rate controllers, e.g., hydroxypropyl cellulose, carboxymethyl cellulose, hydroxypropyl methyl cellulose, ethyl cellulose, methyl cellulose, methyl methacrylate, wax, etc. Other available pharmaceutically acceptable excipients include film forming agents, plasticizers, coloring agents, flavoring agents, viscosity regulators, preservatives, antioxidants, etc. Optionally, tablets are coated with a coating layer in which suitable polymer compound includes hydroxypropylmethylcellulose, polyvinyl alcohol, ethyl cellulose, methacrylic polymer, hydroxypropyl cellulose or starch; anti-adhesive agent includes silica, or talc powder; emulsion agent includes titanium dioxide; and colorant agent includes iron oxide based colorant agent. In the case of liquid oral administration, suitable carriers include water, oils, alcohols, glycols, flavoring agents, preservatives, stabilizers, coloring agents, etc. Aqueous or non-aqueous sterile suspensions may include suspensions and thickeners. Suitable carriers of aqueous suspensions include synthetic gums or natural gums (such as gum Arabic, xanthan gum, alginates, glucans, sodium carboxymethyl cellulose, methylcellulose, polyvinylpyrrolidone or gelatin). In the case of parenteral administration, suitable carriers are usually sterile water, saline or glucose solution. Aqueous or non-aqueous sterile solutions and injections may include buffers, antioxidants, bacteriostatic agents and solutes which can make the pharmaceutical composition isotonic with blood. Each carrier must be acceptable, compatible with other ingredients in the formula and non-hazardous to patients.

The pharmaceutical composition may be prepared by methods commonly known to those skilled in the art. In preparation of the pharmaceutical compositions, canagliflozin Monohydrate, canagliflozin Monohydrate Form HI or canagliflozin Monohydrate Form HII of the present invention is mixed with one or more pharmaceutically acceptable carriers, and optionally with one or more other active pharmaceutical ingredients. Solid dosage forms may be prepared by direct blending, granulation and other processes; liquid dosage forms may be prepared by dissolution, dispersion, emulsification and other processes.

Particularly mentioned is the wet granulation process of solid formulations. Taking the wet granulation process for preparing tablets as an example, the process is: blending dry solids of active ingredients, fillers, adhesives, etc., wetting the mixture with a wetting agent such as water or alcohols, aggregating or granulating the wetted solid, continuing the wet granulation process until the required uniform particle size is obtained, and drying the obtained granules. Then mixing the dried granules with disintegrants, lubricants, anti-adhesives, etc., perform in tableting machine; optionally, coating the tablets with appropriate coating material.

Particularly mentioned is oral suspension. One advantage of the dosage form is that patients do not need to swallow solids, so it is particularly suitable for elders or children who have difficulties in swallowing solids, or patients with oral or throat injuries. Suspension is a two-phase system formed by dispersing solid particles in a liquid, for example, canagliflozin Monohydrate, canagliflozin Monohydrate Form HI or canagliflozin Monohydrate Form HII of the present invention which maintain their original solid forms in water or aqueous carriers in an oral suspension. It is well known to those skilled in the art that other ingredients in the oral suspension may include buffers, surfactants, viscosity regulators, preservatives, antioxidants, coloring agents, flavoring agents, taste masks, etc.

Canagliflozin Monohydrate, canagliflozin Monohydrate Form HI or canagliflozin Monohydrate Form HII of the present invention has a significant effect on controlling the blood sugar. As SGLT inhibitors, they can be used for treating and/or preventing human diseases or disorders related to SGLT. Specifically, according to the objective of the present invention, the present invention provides uses of canagliflozin Monohydrate, canagliflozin Monohydrate Form HI or canagliflozin Monohydrate Form HII of the present invention in the manufacture of drugs for treating and/or preventing diseases and pathologies selected from the group consisting of diabetes, diabetes complications (diabetic retinopathy, diabetic neuropathy, diabetic nephropathy), postprandial hyperglycemia, delayed wound healing, insulin resistance, hyperglycemia, hyperinsulinemia, elevated blood levels of fatty acids, elevated blood levels of glycerol, hyperlipidemia, adiposity, hypertriglyceridemia, syndrome X, atherosclerosis and hypertension.

According to the objective of the present invention, the present invention provides a method for treating and/or preventing diseases selected from the group consisting of diabetes, diabetes complications (diabetic retinopathy, diabetic neuropathy, diabetic nephropathy), postprandial hyperglycemia, delayed wound healing, insulin resistance, hyperglycemia, hyperinsulinemia, elevated blood levels of fatty acids, elevated blood levels of glycerol, hyperlipidemia, adiposity, hypertriglyceridemia, syndrome X, atherosclerosis and hypertension, which comprises administering to a patient in need of a therapeutically and/or preventatively effective amount of canagliflozin Monohydrate, canagliflozin Monohydrate Form HI or canagliflozin Monohydrate Form HII or the pharmaceutical composition of the present invention. The dosage amount depends on administration route, age, body weight, patients' symptoms or types and severity of treating diseases. The dosage amount is in the range of 0.1 to 50 mg/kg/d, preferably 0.1 to 30 mg/kg/d.

EXAMPLES

Figure 1:
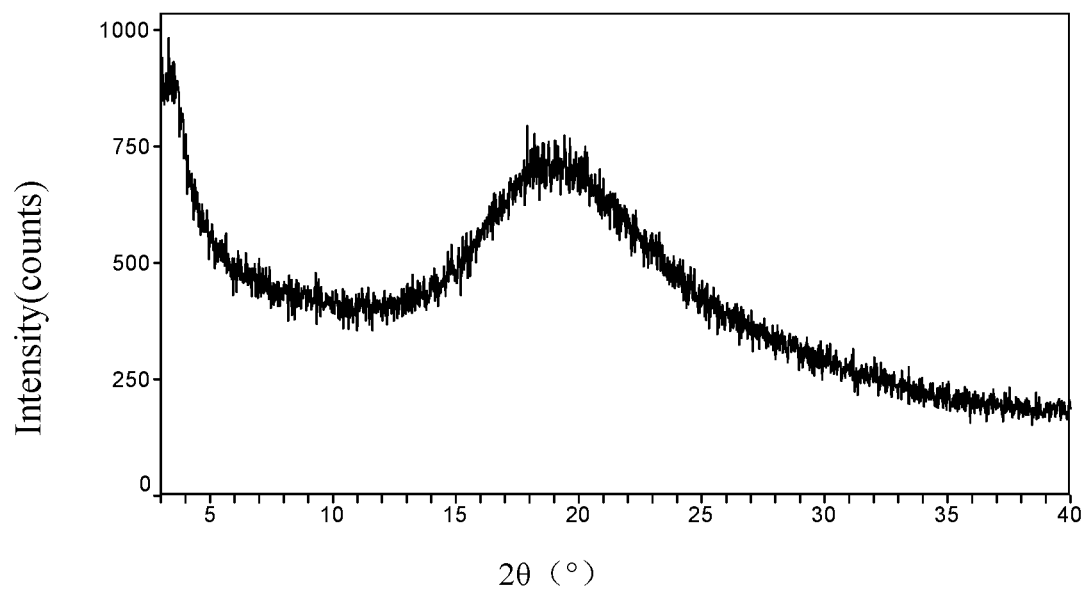
FIG. 1 is the XRPD pattern of canagliflozin amorphous form of preparation example 1.

The present invention further refers to the following examples. These examples describe preparation methods and uses of crystalline forms of the present invention in details. It is apparent to those skilled in the art that various modifications can be made in materials and methods without departing from the scope of the present invention.

Instruments and Methods Used for Data Collection:

X-ray powder diffraction (XRPD) was performed on a Bruker D8 Advance Diffractometer configured with a 0-20 goniometer, a Mo monochrometer and a Lynxeye detector. A Cu-Kα radiation with the wavelength of 1.54 nm operating at 40 kV and 40 mA was used to initiate samples. Before using, the instrument was calibrated using the provided standard (usually corundum). The collection software is DiffracPlus XRPD Commander. The sample was analyzed on a non-reflective plate at room temperature. The detailed testing conditions were: 2θ scan range, 3-40°, step size, 0.02°, speed, 0.2 s/step.

Differential scanning calorimetry (DSC) data were collected using TA Instruments Q200 MDSC. The instrument control software was Thermal Advantage, and the analytical software was Universal Analysis. Usually, 1-10 mg of the sample was placed in an aluminum pan and heated at a rate of 10° C./min from 0° C. to 150° C. under the protection of dry $N_2$ at a flow rate of 40 mL/min.

Thermogravimetric analysis (TGA) data were collected using TA Instruments Q500 TGA. The instrument control software was Thermal Advantage and the analytical software was Universal Analysis. In general, 5-15 mg of the sample was placed in a platinum pan, and by segmental high-resolution detection, the sample was heated at a rate of 10° C./min from room temperature to 300° C. under the protection of dry $N_2$ at a flow rate of 40 mL/min.

Infrared spectrometry (IR) data were collected using BrukerTensor 27. OPUS was used both for instrument control and data analysis. In general, the infrared absorption spectra were collected over 600-4000 $cm^{-1}$ using ATR equipment. Both samples and the blank background were scanned for 16 s. The instrument resolution was 4 $cm^{-1}$.

$^1$H Nuclear magnetic resonance spectrum ($^1$H-NMR) data were collected using Bruker Avance II DMX 400M HZ nuclear magnetic resonance spectrometer. 1-5 mg of sample was dissolved in 0.5 mL of deuterated methanol or deuterium-substituted dimethyl sulfoxide to form a 2 mg/mL-10 mg/mL solution.

Unless particularly specified, all reagents used in the examples were commercially purchased.

Unless particularly specified, all examples were conducted at room temperature which is about 10° C. to 30° C.

Unless particularly specified, ratios of components in the mixed solvents in the examples were volume ratios.

Sonication as used in the examples can promote dissolution of the samples and were operated in the ultrasonic cleaning equipment with 40 Khz for 5 minutes.

Preparation Example 1 (Preparation of the Known Canagliflozin)

The known canagliflozin was prepared in a manner similar to the method disclosed in example 1 in patent document U.S. Pat. No. 7,943,788B2 using a corresponding starting material or according to the following method.

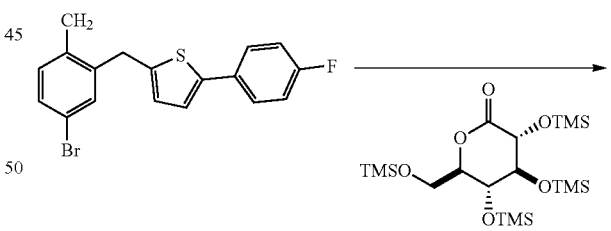

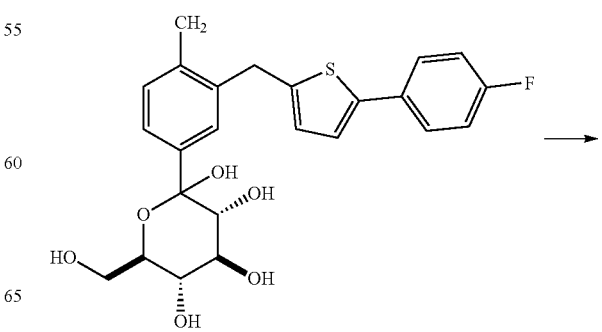

-continued

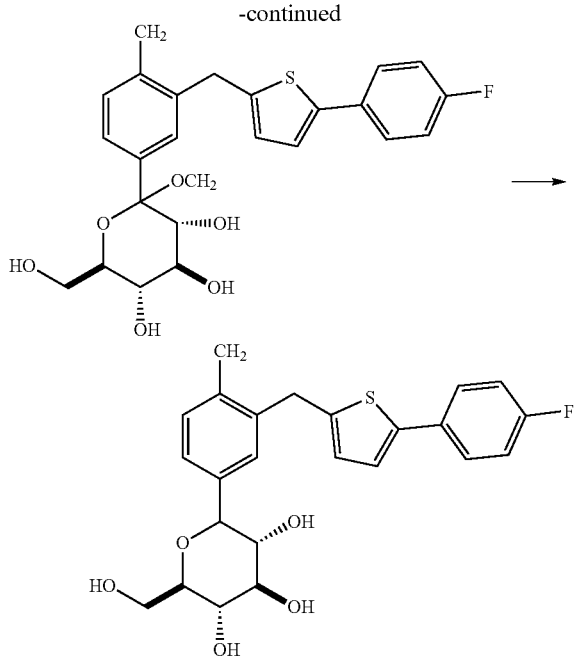

The detailed preparation method is: 5-bromo-1-[5-(4-fluorophenyl)-2-thienylmethyl]-2-methylbenzene (2.65 g) was dissolved in tetrahydrofuran (20 mL)-toluene (40 mL), and the mixture was cooled to −78° C. under argon atmosphere. To the mixture, n-butyl lithium (2.44M hexane solution, 2.9 mL) was added dropwise, and the mixture was stirred at the same temperature for 30 minutes. Then, a solution of 2,3,4,6-tetrakis-O-trimethylsilyl-D-glucono-1,5-lactone (2.3 g) in toluene (50 mL) was added dropwise, and the mixture was further stirred at the same temperature for one hour to give a lactol compound. Without isolating this compound, a solution of methanesulfonic acid (1.0 mL) in methanol (50 mL) was added to the reaction solution, and the mixture was stirred at room temperature overnight. Under ice-cooling, a saturated aqueous solution of sodium hydrogen carbonate was added to the mixture, and the mixture was extracted with ethyl acetate. The extract was washed with brine, dried with magnesium sulfate, and the solvent was evaporated under reduced pressure. The residue was purified by silica gel column chromatography (chloroform:methanol=19:1) to give a methyl ether compound of the lactol. A solution of the above methyl ether compound in dichloromethane (5 mL) was cooled to −78° C. under argon atmosphere, and triisopropylsilane (1.6 mL) and boron trifluoride diethyl ether complex (1.0 mL) were added dropwise. The mixture was stirred at the same temperature for 10 minutes and then warmed up to 0° C. The mixture was stirred at 0° C. for 1 hour and 20 minutes, and then further stirred at room temperature for 2 hours. Under ice-cooling, a saturated aqueous solution of sodium hydrogen carbonate was added, and the mixture was extracted with ethyl acetate. The extract was washed with brine, dried with magnesium sulfate, and the solvent was evaporated under a reduced pressure. The residue was purified by silica gel column chromatography (chloroform:methanol=19:1) to give the desired canagliflozin.

$^1$H-NMR (CD$_3$OD): 2.32 (s, 3H), 3.35-3.53 (m, 4H), 3.71 (d, 1H, J=11.9 Hz), 3.90 (d, 1H, J=11.9 Hz), 4.13 (d, 1H, J=9.3 Hz), 4.17 (s, 2H), 4.9 (s, 4H), 6.70 (d, 1H, J=3.7 Hz), 7.04-7.14 (m, 3H), 7.18 (d, 1H, J=7.8 Hz), 7.26 (d, 1H, J=7.8 Hz), 7.33 (s, 1H), 7.52-7.60 (m, 2H). The $^1$H-NMR data indicates the product is canagliflozin.

The XRPD pattern is shown in FIG. 1, indicating that it is an amorphous form.

Preparation Example 2 (Preparation of the Known Canagliflozin Form A)

The known canagliflozin Form A was prepared according to the methods described in example 9 in patent document WO2009/035969A1.

9.7 g of canagliflozin prepared in the preparation example 1, 0.6 mL of water and 27.5 mL of ethyl acetate were added into a 100 mL three-necked round bottle flask. The resulting solution was heated to 35° C. with stirring under argon atmosphere. Heptane was added dropwise until the solution became hazy (16.0 mL of heptanes). After stirring for 2 hours at 35° C., 3.0 mL of heptane was added. The resulting mixture was stirred for 30 minutes and filtered under a reduced pressure. The filter cake was washed with 5 mL solution of 56% ethyl acetate/44% heptane and dried for 24 hours at 40° C. to obtain canagliflozin Form A.

Figure 2:
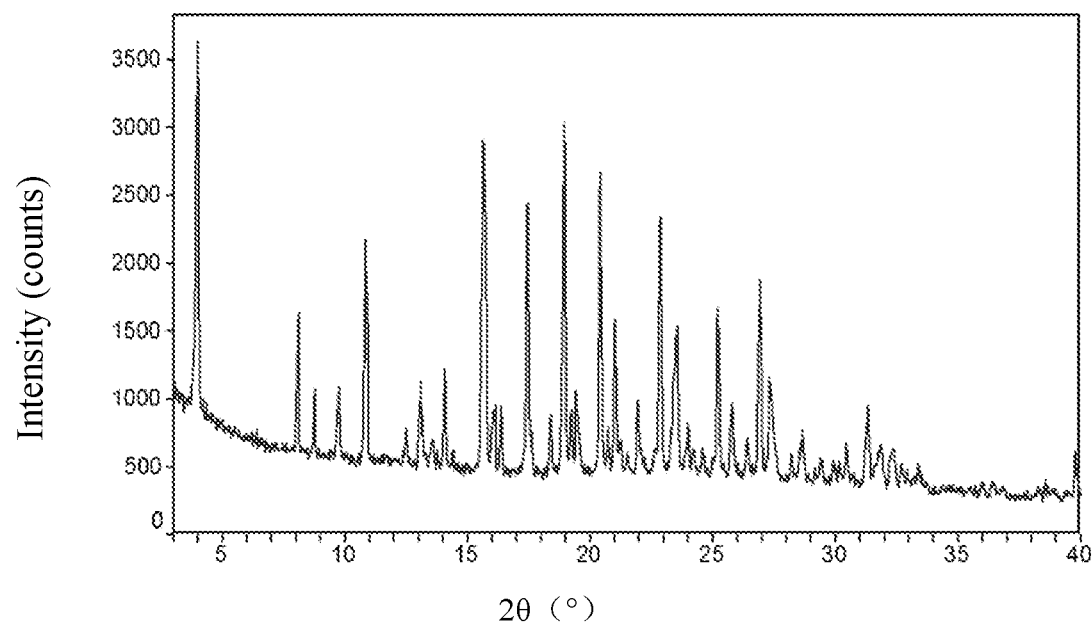
FIG. 2 is the XRPD pattern of canagliflozin Form A of preparation example 2.

$^1$H-NMR (CD$_3$OD): 2.32 (s, 3H), 3.35-3.53 (m, 4H), 3.71 (d, 1H, J=11.9 Hz), 3.90 (d, 1H, J=11.9 Hz), 4.13 (d, 1H, J=9.3 Hz), 4.17 (s, 2H), 4.9 (s, 4H), 6.70 (d, 1H, J=3.7 Hz), 7.04-7.14 (m, 3H), 7.18 (d, 1H, J=7.8 Hz), 7.26 (d, 1H, J=7.8 Hz), 7.33 (s, 1H), 7.52-7.60 (m, 2H). The $^1$H-NMR data indicates that the product is canagliflozin. The XRPD pattern is shown in FIG. 2, indicating that the crystalline form is consistent with canagliflozin Form A disclosed in the patent document WO2009/035969A1.

Preparation Example 3 (Preparation of the Known Canagliflozin Hemihydrate Form hH1)

The known canagliflozin hemihydrate Form hH1 was prepared according to the methods described in example 1 in patent document U.S. Pat. No. 7,943,582B2 or the following method.

The detailed preparation method is as follows: To 1 g of canagliflozin prepared in the preparation example 1, 2.2 mL of water and acetonitrile (10:1) mixed solvent was added. The mixture was stirred at room temperature for 24 hours, filtered under a reduced pressure, dried at 40° C. for 24 hours, and canagliflozin hemihydrate Form hH1 was obtained.

$^1$H-NMR (DMSO-d$_6$) 2.26 (s, 3H), 3.13-3.28 (m, 4H), 3.44 (m, 1H), 3.69 (m, 1H), 3.96 (d, 1H, J=9.3 Hz), 4.10 (m, 1H), 4.15 (m, 1H), 4.43 (t, 1H, J=5.8 Hz), 4.72 (d, 1H, J=5.6 Hz), 4.92 (d, 2H, J=4.8 Hz), 6.80 (d, 1H, J=3.5 Hz), 7.11-7.15 (m, 2H), 7.18-7.25 (m, 3H), 7.28 (d, 1H, J=3.5 Hz), 7.59 (dd, 2H, J=8.8, 5.4 Hz). The $^1$H-NMR data indicates the product is canagliflozin hemihydrate.

Figure 3:
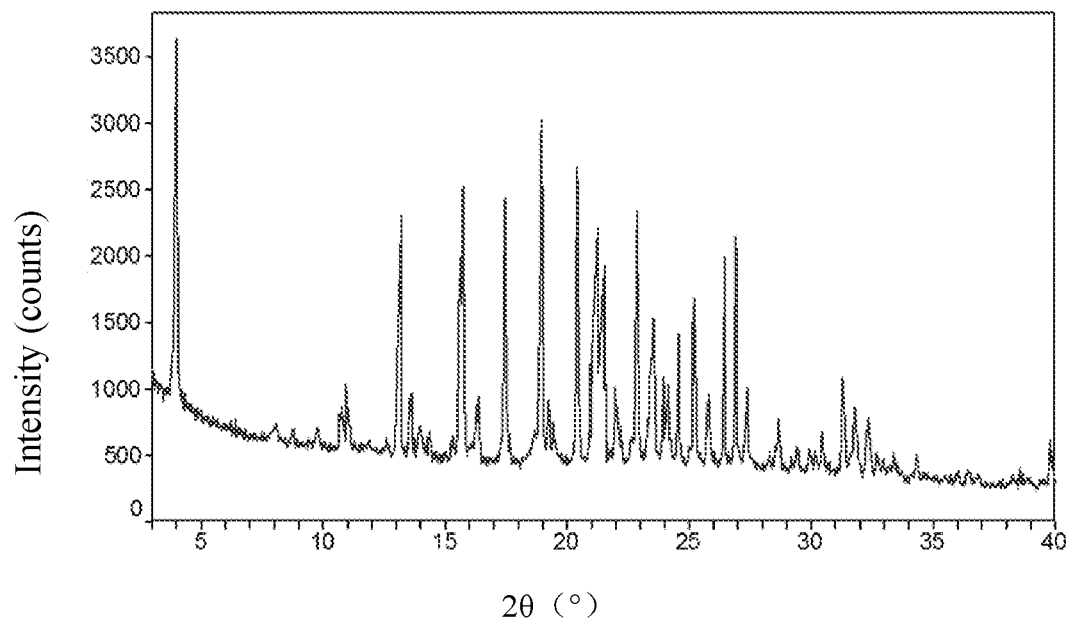
FIG. 3 is the XRPD pattern of canagliflozin hemihydrate Form hH1 of preparation example 3.
Figure 4:
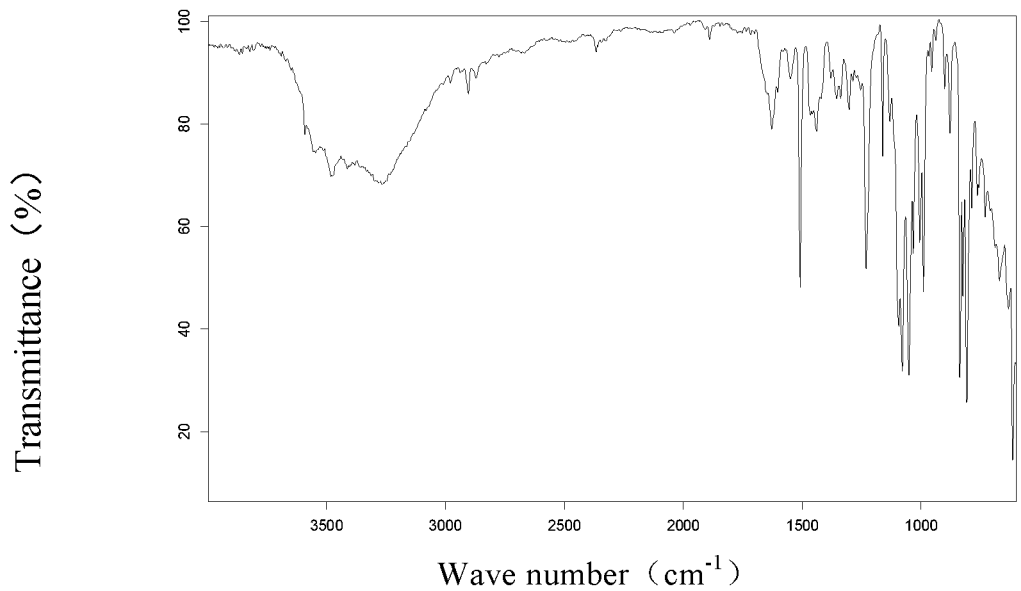
FIG. 4 is the IR spectrum of canagliflozin hemihydrate Form hH1 of example 3.

The XRPD pattern is shown in FIG. 3 and the IR spectrum is shown in FIG. 4, which indicate that the crystalline form is consistent with the canagliflozin hemihydrate Form hH1 disclosed in the patent document U.S. Pat. No. 7,943,582B2.

Example 1 (Preparation of Crystal Seeds of Canagliflozin Monohydrate Form HI)

To 360 mg of canagliflozin prepared in the preparation example 1 in the present invention, a mixed solution consisting of 1.0 ml of solution A (water:isopropanol:cyclohexane=0.3:4:5) and 1.0 ml of cyclohexane was added to form a suspension system. The suspension system was stirred at room temperature for 24 hours, filtered, dried at 35° C. for 8 hours under vacuum, and 350 mg of the canagliflozin Monohydrate Form HI was obtained. The yield was 93.4%.

Figure 5:
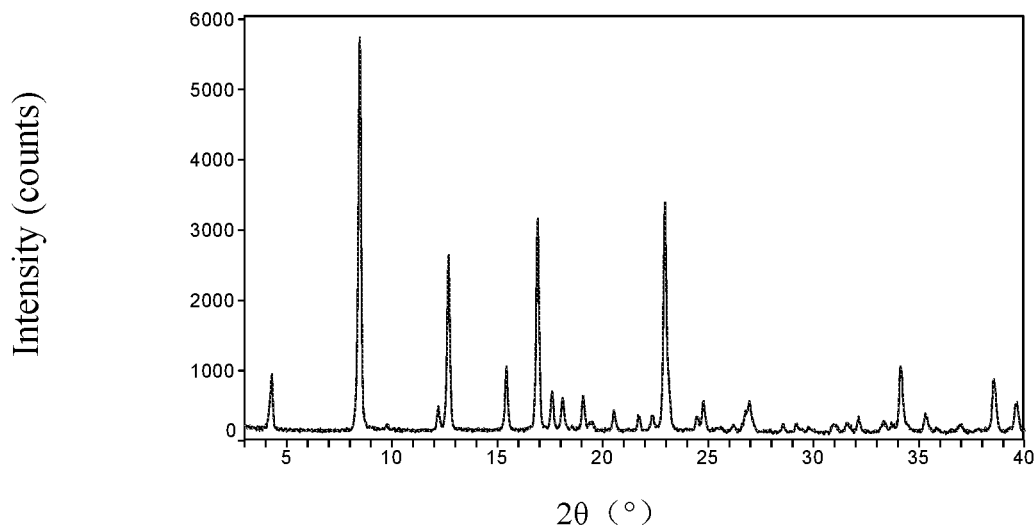
FIG. 5 is the XRPD pattern of canagliflozin Monohydrate Form HI of the present invention.

The XRPD pattern is shown in FIG. 5.

Figure 6:
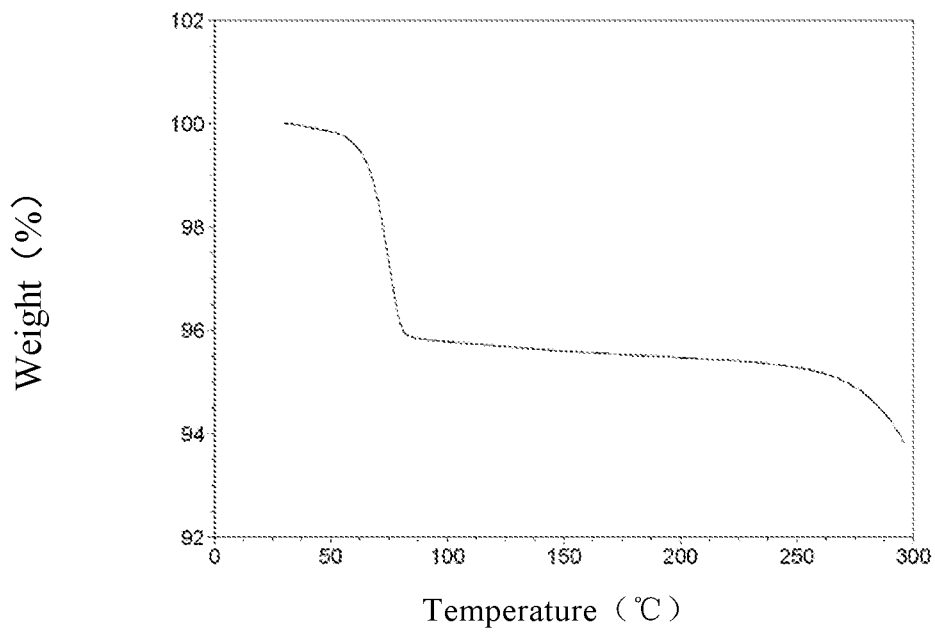
FIG. 6 is the TGA thermogram of canagliflozin Monohydrate Form HI of the present invention.

The TGA thermogram is shown in FIG. 6, indicating that a weight loss of 4.1% occurs before 100° C., which roughly equals the theoretical weight loss of one molecule of water in one molecule of the Monohydrate Form HI.

Example 2

To 500 mg of canagliflozin prepared in the preparation example 1 in the present invention, 2.0 mL of water was added to form a suspension system, 10.0 mg of the crystal seeds prepared in example 1 in the present invention was added into the suspension system, the mixture was stirred at room temperature for 7 days, filtered, dried at 35° C. for 48 hours under vacuum, and 515 mg of canagliflozin Monohydrate Form HI was obtained; the yield was 97.0%.

Example 3

To 500 mg of canagliflozin prepared in the preparation example 1 in the present invention, 5.0 mL of water:acetone:n-heptane (0.2:1:6) mixed solvent was added to form a suspension system, the suspension system was stirred at room temperature for 2 days, filtered, dried at 35° C. for 18 hours under vacuum, and 485 mg of canagliflozin Monohydrate Form HI was obtained, the yield was 93.2%.

Example 4

To 300 mg of canagliflozin prepared in the preparation example 1 in the present invention, 2.0 mL of water:butanol (20:1) mixed solvent was added to form a suspension system, then 15 mg of the crystal seeds prepared in example 1 in the present invention was added, the mixture was stirred at 50° C. for 20 hours, filtered, dried at 50° C. for 2 hours under vacuum, and 312 mg of Canagliflozin Monohydrate Form HI was obtained, the yield was 95.1%.

Example 5

To 1.0 g of canagliflozin prepared in the preparation example 1 in the present invention, 2.0 mL of water:methanol:toluene (0.2:0.8:5) mixed solvent was added to form a suspension system, then 5 mg of the crystal seeds prepared in example 1 in the present invention was added, the mixture was stirred at 15° C. for 3 days, filtered, dried at 35° C. for 10 hours under vacuum, and 980 mg of canagliflozin Monohydrate Form HI was obtained, the yield was 94.2%.

Example 6

To 400 mg of canagliflozin hemihydrate Form hH1 prepared in the preparation example 3 in the present invention, 2.0 mL of water:tetrahydrofuran:butanone (25:1:1) mixed solvent was added to form a suspension system, then 20 mg of the crystal seeds prepared in example 1 in the present invention was added, the mixture was stirred at 30° C. for 6 hours, filtered, dried at 35° C. for 9 hours under vacuum, and 400 mg of canagliflozin Monohydrate form HI was obtained, the yield was 93.2%.

Example 7

To 100 mg of canagliflozin prepared in the preparation example 1 in the present invention, 2 mL of water:ethyl acetate (10:1) mixed solvent was added to form a suspension system, then 10 mg of the crystal seeds prepared in example 1 in the present invention was added, the mixture was grinded at room temperature for 1 hour, filtered, dried at 30° C. for 8 hours under vacuum, and 104 mg of canagliflozin Monohydrate Form HI was obtained, the yield was 90.3%.

Example 8

To 500 mg of canagliflozin hemihydrate form hH1 prepared in the preparation example 3 in the present invention, 2.0 mL of water:1,4-dioxane (15:1) mixed solvent was added to form a suspension system, then 80 mg of the crystal seeds prepared in example 1 in the present invention was added, the mixture was stirred at 20° C. for 24 hours, filtered, dried at 20° C. for 36 hours under vacuum, and 565 mg of canagliflozin Monohydrate Form HI was obtained, the yield was 95.1%.

Example 9

To 400 mg of canagliflozin prepared in the preparation example 1 in the present invention, 2.0 mL of water:acetonitrile:methylcyclohexane (0.3:1:7) mixed solvent was added to form a suspension system, then 20 mg of the crystal seeds prepared in example 1 in the present invention was added, the mixture was stirred at room temperature for 18 hours, filtered, dried at 40° C. for 6 hours under vacuum, and 403 mg of canagliflozin Monohydrate Form HI was obtained, the yield was 92.0%.

Example 10

To 200 mg of canagliflozin prepared in the preparation example 1 in the present invention, 5.0 mL of water:ethanol (10:1) mixed solvent was added to form a suspension system, then 16 mg of the crystal seeds prepared in example 1 in the present invention was added, the mixture was grinded at room temperature for 3 hours, filtered, dried at 35° C. for 18 hours under vacuum, and 210 mg of canagliflozin Monohydrate Form HI was obtained, the yield was 93.2%.

Example 11

To 500 mg of canagliflozin prepared in the preparation example 1 in the present invention, 10.0 mL of water:n-propanol:n-heptane (1:1:5) mixed solvent was added to form a suspension system, then 25 mg of the crystal seeds prepared in example 1 in the present invention was added, the mixture was grinded at room temperature for 0.5 hours, filtered, dried at 40° C. for 5 hours under vacuum, and 517 mg of canagliflozin Monohydrate Form HI was obtained, the yield was 94.6%.

Example 12

To 200 mg of canagliflozin prepared in the preparation example 1 in the present invention, 1 mL of acetone and 8.44, of water were added to form a clear solution, 0.5 mL of n-heptane was added into the solution dropwise under stirring, then 20 mg of the crystal seeds prepared in example 1 in the present invention was added, 9.5 ml of n-heptane continued to be added dropwise. After the addition was completed, the mixture was stirred for crystallization at room temperature for 2 hours, filtered, dried at 35° C. for 7 hours under vacuum, and 212 mg of canagliflozin Monohydrate Form HI was obtained, the yield was 92.2%.

Example 13

To 200 mg of canagliflozin prepared in the preparation example 1 in the present invention, 1 mL of methanol and 50 μL of water were added to form a clear solution, 1.0 mL of n-heptane was added into the solution dropwise under stirring at 45° C., then 20 mg of the crystal seeds prepared in example 1 in the present invention was added, 14.0 mL of n-heptane continued to be added dropwise. After the addition was completed, the mixture was stirred for crystallization at room temperature for 0.5 hours, filtered, dried at 35° C. for 10 hours under vacuum, and 210 mg of canagliflozin Monohydrate Form HI was obtained, the yield was 91.3%.

Example 14

To 400 mg of canagliflozin prepared in the preparation example 1 in the present invention, 1.8 mL of ethanol and 100 μL of water were added to form a clear solution, 4 mL of cyclohexane was added into the solution dropwise under stirring, then 20 mg of the crystal seeds prepared in example 1 in the present invention was also added, 6 mL of cyclohexane continued to be added dropwise. After the addition was completed, the mixture was stirred for crystallization at room temperature for 3 hours, filtered, dried at 40° C. for 11 hours under vacuum, and 382 mg of canagliflozin Monohydrate Form HI was obtained, the yield was 87.0%.

Example 15

To 200 mg of canagliflozin prepared in the preparation example 1 in the present invention, 1.2 mL of butanone and 50 μL of water were added to form a clear solution, the solution was added dropwise into a suspension consisting of 10 mL of nitromethane and 20 mg of the crystal seeds prepared in example 1 in the present invention at 45° C. After the addition was completed, the mixture was stirred for crystallization at room temperature for 24 hours, filtered, dried at 35° C. for 7 hours under vacuum, and 213 mg of canagliflozin Monohydrate Form HI was obtained, the yield was 92.7%

Example 16

To 200 mg of canagliflozin prepared in the preparation example 1 in the present invention, 0.8 mL of 1,4-dioxane and 30 μL of water were added to form a clear solution, the solution was added dropwise into a suspension consisting of 10 mL of water and 20 mg of the crystal seeds prepared in example 1 in the present invention at 5° C. After the addition was completed, the mixture was stirred for crystallization at 5° C. for 5 hours, filtered, dried at 35° C. for 7 hours under vacuum, and 210 mg of Canagliflozin Monohydrate Form HI was obtained, the yield was 91.3%.

Example 17

To 1.0 g of canagliflozin prepared in the preparation example 1 in the present invention, 5 ml of water-saturated ethyl acetate solution was added to form a clear solution, the solution was added dropwise into a suspension consisting of 250 mL of isopropyl ether, 3 mL of water and 5 mg of the crystal seeds prepared in example 1 in the present invention at 15° C. After the addition was completed, the mixture was stirred for crystallization at 15° C. for 1.5 hours, filtered, dried at 40° C. for 7 hours under vacuum, and 925 mg of canagliflozin Monohydrate Form HI was obtained, the yield was 88.4%.

Example 18

To 550 mg of canagliflozin prepared in the preparation example 1 in the present invention, 8.5 mL of methyl tert-butyl ether was added, the mixture was heated to 45° C. to form a clear solution, the solution was added dropwise into a suspension consisting of 200 mL of n-heptane, 3 mL of water and 60 mg of the crystal seeds prepared in example 1 in the present invention. After the addition was completed, the mixture was kept at the temperature and stirred for crystallization for 5 hours, filtered, dried at 35° C. for 4 hours under vacuum, and 547 mg of canagliflozin Monohydrate form HI was obtained, the yield was 85.1%.

Example 19

To 500 mg of canagliflozin hemihydrate Form hH1 prepared in the preparation example 3 in the present invention, 4 mL of tetrahydrofuran and 12 mL of water were added to form a clear solution, the solution was added dropwise into a suspension consisting of 12 mL of water and 100 mg of the crystal seeds prepared in example 1 in the present invention at 20° C. After the addition was completed, the mixture was stirred for crystallization at 20° C. for 4 hours, filtered, dried at 35° C. for 5 hours under vacuum, and 555 mg of canagliflozin Monohydrate Form HI was obtained, the yield was 89.1%.

Example 20

To 400 mg of canagliflozin hemihydrate Form hH1 prepared in the preparation example 3 in the present invention, 3 mL of dichloromethane was added to form a clear solution, the solution and a solution consisting of 30 mL of toluene, 1 mL of water and 4 mg of the crystal seeds prepared in example 1 in the present invention were simultaneously added dropwise into a flask at room temperature. After the addition was completed, the mixture was stirred for crystallization at room temperature for 6 hours, filtered, dried at 35° C. for 5 hours under vacuum, and 374 mg of canagliflozin Monohydrate Form HI was obtained, the yield was 90.7%.

Example 21

To 650 mg of canagliflozin prepared in the preparation example 1 in the present invention, 5 ml of acetonitrile was added to form a clear solution, the solution and 35 mL of water were simultaneously added dropwise into a suspension consisting of 5 mL of water and 65 mg of the crystal seeds prepared in example 1 in the present invention at room temperature. After the addition was completed, the mixture was stirred for crystallization at room temperature for 10 hours, filtered, dried at 35° C. for 3 hours under vacuum, and 665 mg of canagliflozin Monohydrate Form HI was obtained, the yield was 88.7%.

Example 22

To 200 mg of canagliflozin hemihydrate Form hH1 prepared in the preparation example 3 in the present invention, 1 ml of acetone and 1.5 mL of water were added, the mixture was heated to 50° C. to form a clear solution, then the solution was cooled to 30° C. to form a saturated solution of canagliflozin, 10 mg of the crystal seeds prepared in example 1 in the present invention was added, the mixture was further cooled to 5° C., stirred for 2 hours, filtered, dried at 35° C. for 7 hours under vacuum, and 190 mg of canagliflozin Monohydrate Form HI was obtained. The yield was 88.2%.

Example 23

To 500 mg of canagliflozin prepared in the preparation example 1 in the present invention, 2 mL of butanol and 0.5 mL of water were added, the mixture was heated to 80° C. to form a clear solution, the solution was cooled to 45° C. to form a saturated solution of canagliflozin, 100 mg of the crystal seeds prepared in example 1 in the present invention was added, the mixture was further cooled to 30° C., stirred for 24 hours, filtered, dried at 50° C. for 12 hours under vacuum, and 532 mg of canagliflozin Monohydrate Form HI was obtained. The yield was 83.0%.

Example 24

To 600 mg of canagliflozin prepared in the preparation example 1 in the present invention, 3 mL of ethanol and 1.5 mL of water were added, the mixture was heated to 55° C. to form a clear solution, the solution was cooled to 30° C. to form a saturated solution of canagliflozin, 6 mg of the crystal seeds prepared in example 1 in the present invention was added, the mixture was further cooled to 0° C., stirred for 8 hours, filtered, dried at 35° C. for 10 hours under vacuum, and 506 mg of canagliflozin Monohydrate Form HI was obtained. The yield was 80.0%.

Example 25

To 300 mg of canagliflozin prepared in the preparation example 1 in the present invention, 1.5 mL of water-saturated ethyl acetate solution was added, the mixture was heated to 45° C. to form a clear solution, the solution was cooled to 25° C. to form a saturated solution of canagliflozin, 30 mg of the crystal seeds prepared in example 1 in the present invention was added, the mixture was further cooled to −15° C., stirred for 0.5 hours, filtered, dried at 35° C. for 5 hours under vacuum, and 290 mg of canagliflozin Monohydrate Form HI was obtained. The yield was 83.3%.

Example 26

To 500 mg of canagliflozin prepared in the preparation example 1 in the present invention, 2 mL of 1,4-dioxane and 1.0 mL of water were added, the mixture was heated to 80° C. to form a clear solution, the solution was cooled to 25° C. to form a saturated solution of canagliflozin, 50 mg of the crystal seeds prepared in example 1 in the present invention was added, the mixture was further cooled to 15° C., stirred for 5 hours, filtered, dried at 45° C. for 8 hours under vacuum, and 471 mg of canagliflozin Monohydrate Form HI was obtained. The yield was 80.9%.

Example 27

To 550 mg of canagliflozin prepared in the preparation example 1 in the present invention, 3.0 mL of tetrahydrofuran, 0.5 mL of water and 0.5 mL of n-heptane were added, the mixture was heated to 30° C. to form a clear solution, then the solution was cooled to 15° C. to form a saturated solution of canagliflozin, 30 mg of the crystal seeds prepared in example 1 in the present invention was added, the mixture was further cooled to −5° C., stirred for 8 hours, filtered, dried at 35° C. for 5 hours under vacuum, and 515 mg of canagliflozin Monohydrate Form HI was obtained. The yield was 84.8%.

The XRPD patterns and TGA thermograms (not shown) of the samples prepared in examples 2 to 27 were the same as or similar to those of the crystal seeds sample prepared in example 1 in the present invention, indicating that the crystalline forms obtained in examples 2 to 27 were the same crystalline form as that of example 1.

Example 28 (Preparation of the Crystal Seeds of Canagliflozin Monohydrate Form HII)

To 50 mg of canagliflozin prepared in the preparation example 1 in the present invention, 3.0 mL of water and acetonitrile (1:2) mixed solvent was added, the mixture was sonicated at 40° C. to form a clear solution (the concentration of the canagliflozin solution is 0.8 time of its solubility in the mixed solvent of water and acetonitrile (1:2)), 2.5 mg of hydroxypropyl cellulose (average molecular weight 50,000) was added to form a solution system, the solution system was volatilized under atmospheric conditions for crystallization for 1 day, filtered under reduced pressure, washed with 3.0 mL of water, dried at 30° C. for 10 hours, and 49.0 mg of canagliflozin Monohydrate Form HII was obtained. The yield was 94.2%.

Figure 7:
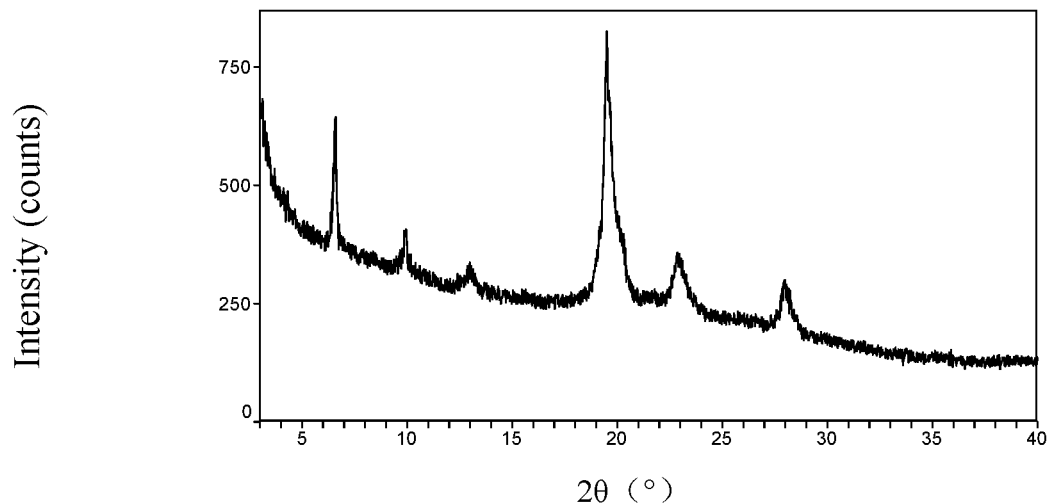
FIG. 7 is the XRPD pattern of canagliflozin Monohydrate Form HII of the present invention.

The XRPD pattern is shown in FIG. 7.

Figure 8:
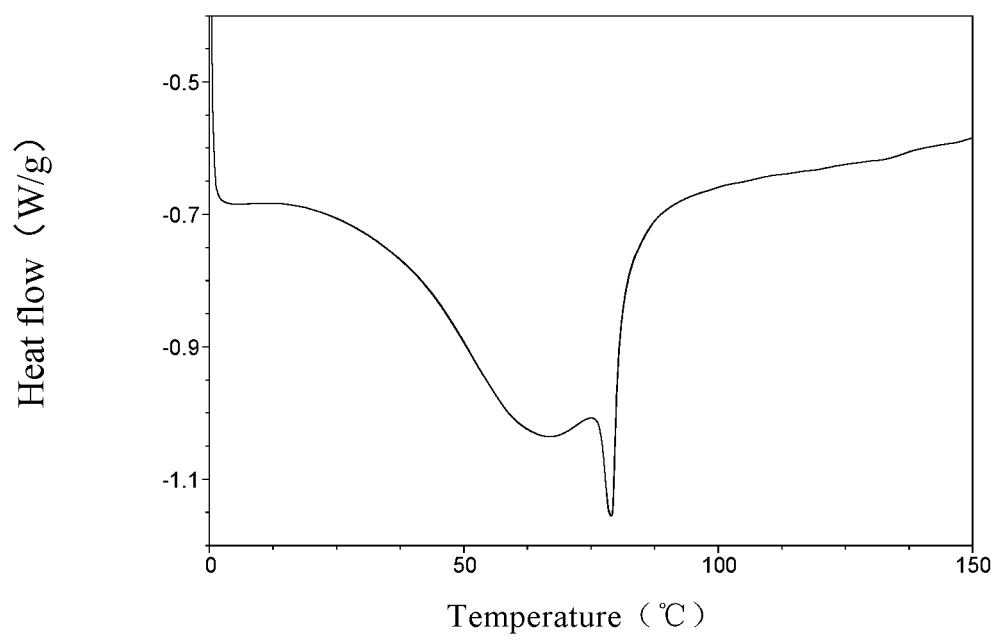
FIG. 8 is the DSC thermogram of canagliflozin Monohydrate Form HII of the present invention.

The DSC thermogram is shown in FIG. 8.

Figure 9:
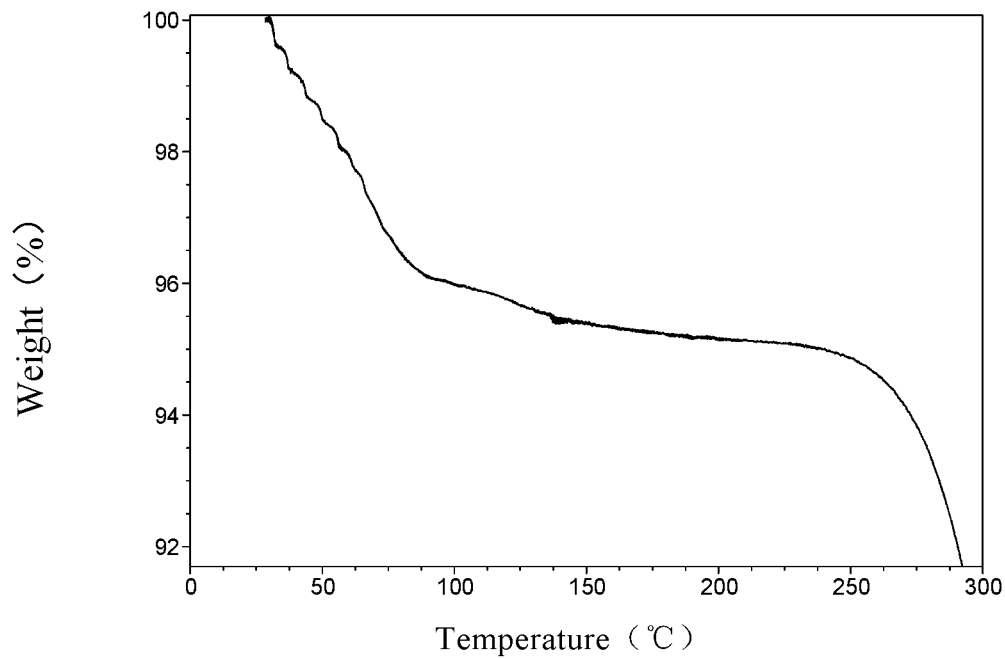
FIG. 9 is the TGA thermogram of canagliflozin Monohydrate Form HII of the present invention.

The TGA thermogram is shown in FIG. 9, indicating that a weight loss of 4.1% occurs before 100° C., which roughly equals to the theoretical weight loss of one molecular of water in one molecule of the Monohydrate Form HII.

Figure 10:
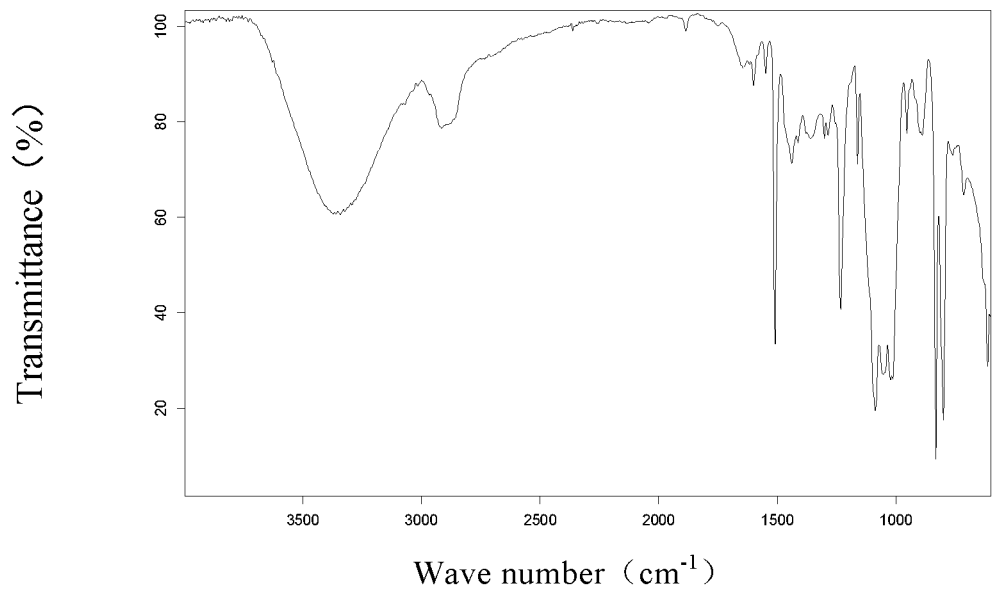
FIG. 10 is the IR spectrum of canagliflozin Monohydrate Form HII of the present invention.

The IR spectrum is shown in FIG. 10.

Example 29

To 70 mg of canagliflozin prepared in the preparation example 1 in the present invention, 3.0 mL of water:acetonitrile (1:3) mixed solvent was added, the mixture was sonicated at 30° C. to form a clear solution (the concentration of the canagliflozin solution is 1 time of its solubility in water:acetonitrile (1:3) mixed solvent), 1.4 mg of hydroxypropyl cellulose (molecular weight 1,000,000) was added to form a solution system, the solution system was volatilized under atmospheric conditions for crystallization for 3 days, filtered under reduced pressure, washed with 2.4 mL of ethanol, dried at 20° C. for 16 hours, and 69.1 mg of canagliflozin Monohydrate Form HII was obtained. The yield was 94.9%.

Example 30

To 30 mg of canagliflozin hemihydrate Form hH1 prepared in the preparation example 3 in the present invention, 3.0 mL of water:acetone (1:4) mixed solvent was added, the mixture was sonicated at 50° C. to form a clear solution (the concentration of the canagliflozin solution is 0.2 time of its solubility in water:acetone (1:4) mixed solvent), 2.4 mg of hydroxypropyl cellulose (molecular weight 1,250,000) was added to the solution to form a suspension system, the suspension system was volatilized under atmospheric conditions for crystallization for 2 days, filtered under reduced pressure, washed with 1.0 mL of water, dried at 10° C. for 48 hours, and 24.3 mg of canagliflozin Monohydrate Form HII was obtained. The yield was 79.4%.

Example 31

To 48 mg of canagliflozin prepared in the preparation example 1 in the present invention, 5.0 mL of water:acetone (1:3) mixed solvent was added, the mixture was sonicated at 35° C. to form a clear solution (the concentration of the canagliflozin solution is 1 time of its solubility in water:acetone (1:3) mixed solvent), 1.9 mg of hydroxypropylmethylcellulose (molecular weight 10,000) was added to the solution to form a solution system, the solution system was volatilized under atmospheric conditions for crystallization for 1 day, filtered under reduced pressure, washed with 1.5 mL of ethanol and 3.0 mL of water, dried at 28° C. for 12 hours, and 46.5 mg of Canagliflozin Monohydrate Form HII was obtained. The yield was 93.0%.

Example 32

To 32 mg of canagliflozin prepared in the preparation example 1 in the present invention, 5.0 mL of water:acetone (1:1) mixed solvent was added, the mixture was sonicated at 20° C. to form a clear solution (the concentration of the canagliflozin solution is 0.8 time of its solubility in water:acetone (1:1) mixed solvent), 1.6 mg of hydroxypropylmethylcellulose (molecular weight 1,000,000) was added to the solution to form a solution system, the solution system was volatilized under atmospheric conditions for crystallization for 5 days, filtered under reduced pressure, washed with 1.5 mL of ethanol and 2.5 mL of water, dried at 30° C. for 18 hours, and 30.2 mg of canagliflozin Monohydrate Form HII was obtained. The yield was 90.7%.

Example 33

To 10 mg of canagliflozin prepared in the preparation example 1 in the present invention, 5.0 mL of water:ethanol (4:1) mixed solvent was added, the mixture was sonicated at 30° C. to form a clear solution (the concentration of the canagliflozin solution is 0.2 time of its solubility in water:ethanol (4:1) mixed solvent), 1.0 mg of hydroxypropylmethylcellulose (molecular weight 1,500,000) was added to the solution to form a solution system, the solution system was volatilized under atmospheric conditions for crystallization for 1 day, filtered under reduced pressure, washed with 1.5 mL of ethanol and 3.5 mL of water, dried at 10° C. for 40 hours, and 7.4 mg of canagliflozin Monohydrate Form HII was obtained. The yield was 71.1%.

Example 34

To 46 mg of canagliflozin prepared in the preparation example 1 in the present invention, 5.0 mL of water:ethanol (1:3) mixed solvent was added, the mixture was sonicated at 30° C. to form a clear solution (the concentration of the canagliflozin solution is 0.9 time of its solubility in water:ethanol (1:3) mixed solvent), 1.4 mg of polyethylene glycol (molecular weight 200) was added to the solution to form a solution system, the solution system was volatilized under atmospheric conditions for crystallization for 2 days, filtered under reduced pressure, washed with 4.5 mL of water, dried at 25° C. for 15 hours, and 44.2 mg of canagliflozin Monohydrate Form HII was obtained. The yield was 92.4%.

Example 35

To 55 mg of canagliflozin prepared in the preparation example 1 in the present invention, 5.0 mL of water:ethanol (1:4) mixed solvent was added, the mixture was sonicated at 40° C. to form a clear solution (the concentration of the canagliflozin solution is 1 time of its solubility in water:ethanol (1:4) mixed solvent), 1.1 mg of polyethylene glycol (molecular weight 2,000) was added to the solution to form a solution system, the solution system was volatilized under atmospheric conditions for crystallization for 2 days, filtered under reduced pressure, washed with 4.0 mL of ethanol, dried at 30° C. for 10 hours, and 51.9 mg of canagliflozin Monohydrate Form HII was obtained. The yield was 90.7%.

Example 36

To 10 mg of canagliflozin prepared in the preparation example 1 in the present invention, 5.0 mL of water:isopropanol (2:1) mixed solvent was added, the mixture was sonicated at 20° C. to form a clear solution (the concentration of the canagliflozin solution is 0.4 time of its solubility in water:isopropanol (2:1) mixed solvent), 1.0 mg of polyethylene glycol (molecular weight 8,000) was added to the solution to form a solution system, the solution system was volatilized under atmospheric conditions for crystallization for 2 days, filtered under reduced pressure, washed with 1.5 mL of ethanol, dried at 40° C. for 13 hours, and 6.9 mg of canagliflozin Monohydrate Form HII was obtained. The yield was 66.3%.

Example 37

To 54 mg of canagliflozin prepared in the preparation example 1 in the present invention, 5.0 mL of water:2-butanol (1:1) mixed solvent was added, the mixture was sonicated at 20° C. to form a clear solution (the concentration of the canagliflozin solution is 0.5 time of its solubility in water: 2-butanol (1:1) mixed solvent), 1.1 mg of polyvinylpyrrolidone (molecular weight 5,000) was added to the solution to form a solution system, the solution system was volatilized under atmospheric conditions for crystallization for 2 days, filtered under reduced pressure, washed with 4 mL of water, dried at 20° C. for 24 hours, and 51.0 mg of canagliflozin Monohydrate Form HII was obtained. The yield was 90.7%.

Example 38

To 180 mg of canagliflozin prepared in the preparation example 1 in the present invention, 5.0 mL of water:isopropanol (1:3) mixed solvent was added, the mixture was sonicated at 30° C. to form a clear solution (the concentration of the canagliflozin solution is 1 time of its solubility in water:isopropanol (1:3) mixed solvent), 7.2 mg of polyvinylpyrrolidone (molecular weight 6000) was added to the solution to form a solution system, the solution system was volatilized under atmospheric conditions for crystallization for 1 day, filtered under reduced pressure, washed with 5 mL of water, dried at 25° C. for 20 hours, and 173.1 mg of canagliflozin Monohydrate Form HII was obtained. The yield was 92.4%.

Example 39

To 120 mg of canagliflozin prepared in the preparation example 1 in the present invention, 5.0 mL of water:isopropanol (1:2) mixed solvent was added, the mixture was sonicated at 40° C. to form a clear solution (the concentration of the canagliflozin solution is 0.8 time of its solubility in water:isopropanol (1:2) mixed solvent), 6.0 mg of polyvinylpyrrolidone (molecular weight 7000) was added to the solution to form a solution system, the solution system was volatilized under atmospheric conditions for crystallization for 3 days, filtered under reduced pressure, washed with 1.5 mL of water, dried at 10° C. for 45 hours, and 110.2 mg of canagliflozin Monohydrate Form HII was obtained. The yield was 88.3%.

Example 40

To 30 mg of canagliflozin prepared in the preparation example 1 in the present invention, 5.0 mL of water:methanol (1:4) mixed solvent was added, the mixture was sonicated at 60° C. to form a clear solution (the concentration of the canagliflozin solution is 0.4 time of its solubility in water:methanol (1:2) mixed solvent), 1.8 mg of sodium carboxymethyl cellulose (molecular weight 90,000) dissolved in 1.0 mL of water:methanol (1:4) mixed solvent was added to the solution to form a suspension system, the suspension system was volatilized under atmospheric conditions for crystallization for 3 days, filtered under reduced pressure, washed with 3.5 mL of water, dried at 40° C. for 28 hours, and 25.2 mg of canagliflozin Monohydrate Form HII was obtained. The yield was 80.7%.

Example 41

To 40 mg of canagliflozin prepared in the preparation example 1 in the present invention, 5.0 mL of water:methanol (1:1) mixed solvent was added, the mixture was sonicated at 40° C. to form a clear solution (the concentration of the canagliflozin solution is 1 time of its solubility in water:methanol (1:1) mixed solvent), 1.0 mg of sodium carboxymethyl cellulose (molecular weight 300,000) dissolved in 1.0 mL of water:methanol (1:1) mixed solvent was added to the solution to form a suspension system, the suspension system was volatilized under atmospheric conditions for crystallization for 2 days, filtered under reduced pressure, washed with 5 mL of water, dried at 30° C. for 24 hours, and 38.7 mg of canagliflozin Monohydrate Form HII was obtained. The yield was 93.0%.

Example 42

To 15 mg of canagliflozin prepared in the preparation example 1 in the present invention, 5.0 mL of water:acetonitrile (4:1) mixed solvent was added, the mixture was sonicated at 20° C. to form a clear solution (the concentration of the canagliflozin solution is 0.5 time of its solubility in water:acetonitrile (4:1) mixed solvent), 1.0 mg of sodium carboxymethyl cellulose (molecular weight 700,000) dissolved in 1.0 mL of water:acetonitrile (4:1) mixed solvent was added to the solution to form a suspension system, the suspension system was volatilized under atmospheric conditions for crystallization for 4 days, filtered under reduced pressure, washed with 1.5 mL of water, dried at 10° C. for 46 hours, and 13.1 mg of canagliflozin Monohydrate Form HII was obtained. The yield was 83.9%.

Example 43

To 12 mg of canagliflozin prepared in the preparation example 1 in the present invention, 5.0 mL of water:n-butanol (2:1) mixed solvent was added, the mixture was sonicated at 50° C. to form a clear solution (the concentration of the canagliflozin solution is 0.4 time of its solubility in water:n-butanol (2:1) mixed solvent), 0.8 mg of Carbomer (molecular weight 1,000,000) dissolved in 0.8 mL of water:n-butanol (2:1) mixed solvent was added to the solution to form a solution system, the solution system was volatilized under atmospheric conditions for crystallization for 4 days, filtered under reduced pressure, washed with 3.0 mL of water, dried at 18° C. for 33 hours, and 9.9 mg of canagliflozin Monohydrate Form HII was obtained. The yield was 79.3%.

Example 44

To 60 mg of canagliflozin prepared in the preparation example 1 in the present invention, 5.0 mL of water:n-butanol (1:3) mixed solvent was added, the mixture was sonicated at 30° C. to form a clear solution (the concentration of the canagliflozin solution is 1 time of its solubility in water:n-butanol (1:3) mixed solvent), 1.2 mg of Carbomer (molecular weight 2,000,000) dissolved in 0.8 mL of water:n-butanol (1:3) mixed solvent was added to the solution to form a solution system, the solution system was volatilized under atmospheric conditions for crystallization for 2 days, filtered under reduced pressure, washed with 5.0 mL of water, dried at 30° C. for 16 hours, and 57.8 mg of canagliflozin Monohydrate Form HII was obtained. The yield was 92.6%.

Example 45

To 30 mg of canagliflozin prepared in the preparation example 1 in the present invention, 5.0 mL of water:n-butanol (1:2) mixed solvent was added, the mixture was sonicated at 20° C. to form a clear solution (the concentration of the canagliflozin solution is 0.8 time of its solubility in water:n-butanol (1:2) mixed solvent), 1.5 mg of Carbomer (molecular weight 4,000,000) dissolved in 0.8 mL of water:n-butanol (1:2) mixed solvent was added to the solution to form a solution system, the solution system was volatilized under atmospheric conditions for crystallization for 3 days, filtered under reduced pressure, washed with 4.5 mL of water, dried at 20° C. for 18 hours, and 27.9 mg of canagliflozin Monohydrate Form HII was obtained. The yield was 89.4%.

Example 46

To 48 mg of canagliflozin prepared in the preparation example 1 in the present invention, 5.0 mL of water:butanone (3:1) mixed solvent was added, the mixture was sonicated at 15° C. to form a clear solution (the concentration of the canagliflozin solution is 0.3 time of its solubility in water:butanone (3:1) mixed solvent), 4.3 mg of ethyl cellulose (the ethoxyl content being 44%) dissolved in 0.5 mL of water:butanone (3:1) mixed solvent was added to the solution to form a suspension system, the suspension system was volatilized under atmospheric conditions for crystallization for 5 days, filtered under reduced pressure, washed with 2.5 mL of tetrahydrofuran, dried at 15° C. for 45 hours, and 39.6 mg of canagliflozin Monohydrate Form HII was obtained. The yield was 79.3%.

Example 47

To 200 mg of canagliflozin prepared in the preparation example 1 in the present invention, 5.0 mL of water:butanone (1:1) mixed solvent was added, the mixture was sonicated at 40° C. to form a clear solution (the concentration of the canagliflozin solution is 1 time of its solubility in water:butanone (1:1) mixed solvent), 4.0 mg of ethyl cellulose (the ethoxyl content is 48%) dissolved in 0.5 mL of water:butanone (1:1) mixed solvent was added to the solution to form a suspension system, the suspension system was volatilized under atmospheric conditions for crystallization for 5 days, filtered under reduced pressure, washed with 3.0 mL of ethyl acetate, dried at 40° C. for 12 hours, and 190.5 mg of canagliflozin Monohydrate Form HII was obtained. The yield was 91.5%.

Example 48

To 180 mg of canagliflozin prepared in the preparation example 1 in the present invention, 5.0 mL of water:butanone (1:3) mixed solvent was added, the mixture was sonicated at 20° C. to form a clear solution (the concentration of the canagliflozin solution is 0.5 time of its solubility in water:butanone (1:3) mixed solvent), 9.0 mg of ethyl cellulose (the ethoxyl content is 51%) dissolved in 0.5 mL of water:butanone (1:3) mixed solvent was added to the solution to form a suspension system, the suspension system was volatilized under atmospheric conditions for crystallization for 5 days, filtered under reduced pressure, washed with 2.0 mL of ethyl acetate, dried at 30° C. for 15 hours, and 155.4 mg of canagliflozin Monohydrate Form HII was obtained. The yield was 83.0%.

Example 49

To 18 mg of canagliflozin prepared in the preparation example 1 in the present invention, 5.0 mL of water:1,4-dioxane (4:1) mixed solvent was added, the mixture was sonicated at 10° C. to form a clear solution (the concentration of the canagliflozin solution is 0.2 time of its solubility in water:1,4-dioxane (4:1) mixed solvent), 1.8 mg of polymethylmethacrylate (molecular weight 300,000) dissolved in 0.2 mL of water:1,4-dioxane (4:1) mixed solvent was added to the solution to form a suspension system, the suspension system was volatilized under atmospheric conditions for crystallization for 5 days, filtered under reduced pressure, washed with 1.5 mL of ethyl acetate, dried at 10° C. for 48 hours, and 14.5 mg of canagliflozin Monohydrate Form HII was obtained. The yield was 77.4%.

Example 50

To 150 mg of canagliflozin prepared in the preparation example 1 in the present invention, 5.0 mL of water:1,4-dioxane (1:1) mixed solvent was added, the mixture was sonicated at 40° C. to form a clear solution (the concentration of the canagliflozin solution is 1 time of its solubility in water:1,4-dioxane (1:1) mixed solvent), 3.0 mg of polymethylmethacrylate (its molecular weight is 400,000) dissolved in 0.2 mL of water: 1,4-dioxane (1:1) mixed solvent was added to the solution to form a suspension system, the suspension system was volatilized under atmospheric conditions for crystallization for 1 day, filtered under reduced pressure, washed with 5.0 mL of ethyl acetate, dried at 20° C. for 24 hours, and 144.9 mg of canagliflozin Monohydrate Form HII was obtained. The yield was 92.8%.

Example 51

To 60 mg of canagliflozin prepared in the preparation example 1 in the present invention, 5.0 mL of water:1,4-dioxane (2:1) mixed solvent was added, the mixture was sonicated at 20° C. to form a clear solution (the concentration of the canagliflozin solution is 0.5 time of its solubility in water:1,4-dioxane (2:1) mixed solvent), 1.8 mg of polymethylmethacrylate (molecular weight 450,000) dissolved in 0.2 mL of water:1,4-dioxane (2:1) mixed solvent was added to the solution to form a suspension system, the suspension system was volatilized under atmospheric conditions for crystallization for 3 days, filtered under reduced pressure, washed with 3.0 mL of ethyl acetate, dried at 25° C. for 16 hours, and 51.7 mg of canagliflozin Monohydrate Form HII was obtained. The yield was 82.8%.

Example 52

To 45 mg of canagliflozin prepared in the preparation example 1 in the present invention, 5.0 mL of water:n-propanol (1:3) mixed solvent was added, the mixture was sonicated at 40° C. to form a clear solution (the concentration of the canagliflozin solution is 1 time of its solubility in water:n-propanol (1:3) mixed solvent), 1.0 mg of Poloxamer (molecular weight 1000) dissolved in 0.2 mL of water:n-propanol (1:3) mixed solvent was added to the solution to form a solution system, the solution system was volatilized under atmospheric conditions for crystallization for 1 day, filtered under reduced pressure, washed with 5.0 mL of ethyl acetate, dried at 20° C. for 24 hours, and 43.2 mg of canagliflozin Monohydrate Form HII was obtained. The yield was 92.3%.

Example 53

To 100 mg of canagliflozin prepared in the preparation example 1 in the present invention, 5.0 mL of water:2-butanol (1:1) mixed solvent was added, the mixture was sonicated at 60° C. to form a clear solution (the concentration of the canagliflozin solution is 0.5 time of its solubility in water:1,4-dioxane (1:1) mixed solvent), 5.0 mg of Poloxamer (molecular weight 10000) dissolved in 0.2 mL of water:1,4-dioxane (1:1) mixed solvent was added to the solution to form a solution system, the solution system was volatilized under atmospheric conditions for crystallization for 3 days, filtered under reduced pressure, washed with 3.0 mL of ethyl acetate, dried at 30° C. for 18 hours, and 94.1 mg of canagliflozin Monohydrate Form HII was obtained. The yield was 90.4%.

Example 54

To 20 mg of canagliflozin prepared in the preparation example 1 in the present invention, 5.0 mL of water:n-propanol (2:1) mixed solvent was added, the mixture was sonicated at 10° C. to form a clear solution (the concentration of the canagliflozin solution is 0.2 time of its solubility in water:1,4-dioxane (2:1) mixed solvent), 2.0 mg of Poloxamer (molecular weight 16000) dissolved in 0.2 mL of water:1,4-dioxane (2:1) mixed solvent was added to the solution to form a solution system, the solution system was volatilized under atmospheric conditions for crystallization for 5 days, filtered under reduced pressure, washed with 1.5 mL of ethyl acetate, dried at 10° C. for 48 hours, and 14.8 mg of canagliflozin Monohydrate Form HII was obtained. The yield was 71.1%.

Example 55

To 70 mg of canagliflozin prepared in the preparation example 1 in the present invention, 3.0 mL of water:acetonitrile (1:3) mixed solvent was added, the mixture was sonicated at 30° C. to form a clear solution (the concentration of the canagliflozin solution is 1 time of its solubility in water:acetonitrile (1:3) mixed solvent), 7 mg of the crystal seeds of canagliflozin Monohydrate Form HII prepared in example 28 was added to the solution to form a suspension system, the suspension system was volatilized under atmospheric conditions for crystallization for 2 days, filtered under reduced pressure, washed with 3 mL of water, dried at 20° C. for 20 hours, and 68.5 mg of canagliflozin Monohydrate Form HII was obtained. The yield was 84.4%.

Example 56

To 30 mg of canagliflozin hemihydrate Form hH1 prepared in the preparation example 3 in the present invention, 5.0 mL of water:n-butanol (1:2) mixed solvent was added, the mixture was sonicated at 20° C. to form a clear solution (the concentration of the canagliflozin solution is 0.8 time of its solubility in water:n-butanol (1:2) mixed solvent), 2.4 mg of the crystal seeds of canagliflozin Monohydrate Form HII prepared in example 28 was added to the solution to form a suspension system, the suspension system was volatilized under atmospheric conditions for crystallization for 3 days, filtered under reduced pressure, washed with 4.0 mL of water, dried at 22° C. for 18 hours, and 28.8 mg of canagliflozin Monohydrate Form HII was obtained. The yield was 86.3%.

Example 57

To 60 mg of canagliflozin prepared in the preparation example 1 in the present invention, 5.0 mL of water:1,4-dioxane (2:1) mixed solvent was added, the mixture was sonicated at 20° C. to form a clear solution (the concentration of the canagliflozin solution is 0.5 time of its solubility in water:1,4-dioxane (2:1) mixed solvent), 3 mg of the crystal seeds of canagliflozin Monohydrate Form HII prepared in example 28 was added to the solution to form a suspension system, the suspension system was volatilized under atmospheric conditions for crystallization for 4 days, filtered under reduced pressure, washed with 3.0 mL of water, dried at 15° C. for 30 hours, and 54.2 mg of canagliflozin Monohydrate Form HII was obtained. The yield was 82.0%.

Example 58

To 180 mg of canagliflozin prepared in the preparation example 1 in the present invention, 5.0 mL of water:butanone (1:3) mixed solvent was added, the mixture was sonicated at 20° C. to form a clear solution (the concentration of the canagliflozin solution is 0.5 time of its solubility in water:butanone (1:3) mixed solvent), 3.6 mg of the crystal seeds of canagliflozin Monohydrate Form HII prepared in example 28 was added to the solution to form a suspension system, the suspension system was volatilized under atmospheric conditions for crystallization for 5 days, filtered under reduced pressure, washed with 2.0 mL of water, dried at 30° C. for 11 hours, and 154.9 mg of canagliflozin Monohydrate Form HII was obtained. The yield was 80.8%.

Example 59

100 mg of canagliflozin prepared in the preparation example 1 in the present invention was placed in a desiccator at room temperature and 75% RH for 1 day, and 103.6 mg of Canagliflozin Monohydrate Form HII was obtained. The yield was 99.6%.

Example 60

80 mg of canagliflozin prepared in the preparation example 1 in the present invention was placed in a constant temperature and humidity chamber at room temperature and 68% RH for 2 days, and 82.4 mg of canagliflozin Monohydrate Form HII was obtained. The yield was 99.0%.

Example 61

120 mg of canagliflozin prepared in the preparation example 1 in the present invention was placed in a desiccator at room temperature and 75% RH for 3 days, and 123.2 mg of canagliflozin Monohydrate Form HII was obtained. The yield was 98.7%.

The XRPD patterns, IR spectra, DSC thermograms and TGA thermograms (not shown) of the samples prepared in examples 29 to 61 were the same as or similar to those of the crystal seeds sample prepared in example 28, indicating that the crystalline forms obtained in examples 29 to 61 were the same crystalline forms as that of example 28.

Example 62 Preparation of Tablets

Tablets were prepared with canagliflozin Monohydrate Form HI or canagliflozin Monohydrate Form HII of the present invention as the active pharmaceutical ingredient, and each tablet contained 100 mg of canagliflozin. The formula of the tablets was as follows:

Canagliflozin Monohydrate Form HI or canagliflozin Monohydrate Form HII of the present invention: 104.0 mg/tablet
D-mannitol: 16.0 mg/tablet
Hydroxypropyl cellulose: 4.0 mg/tablet
Cross-linked sodium carboxymethyl cellulose: 5.6 mg/tablet
Talc powder: 1.4 mg/tablet
Sodium stearyl fumarate: 4.0 mg/tablet
Total: 135 mg/tablet Preparation Procedures of the Tablets (Scale: 10,000 Tablets) were as Follows:

1) Pass cross-linked sodium carboxymethyl cellulose, talc powder and sodium stearyl fumarate through a 22-mesh sieve.

2) Thoroughly mix canagliflozin Monohydrate Form HI or canagliflozin Monohydrate Form HII of the present invention, D-mannitol and hydroxypropyl cellulose in a mixer, and granulate using 11.9 mg of water per tablet as the wetting agent.

3) Dry the wet granules in an oven until the water content is less than 3%, pass the dried granules through a 22-mesh sieve, add cross-linked sodium carboxymethyl cellulose, talc powder and sodium stearyl fumarate prepared in step 1) to the sieved dry granules and mix well. Analyze the active ingredient in the granules, determine the tablet target weight and then perform tableting. A total of 10.000 tablets were made.

Example 63 Preparation of Tablets

Tablets were prepared with canagliflozin Monohydrate Form HI or canagliflozin Monohydrate Form HII of the present invention as the active pharmaceutical ingredient, and each tablet contained 300 mg of canagliflozin. The formula of tablets was as follows:
Canagliflozin Monohydrate Form HI or canagliflozin Monohydrate Form HII of the present invention: 312.0 mg/tablet
D-mannitol: 48.0 mg/tablet
Hydroxypropyl cellulose: 12.0 mg/tablet
Cross-linked sodium carboxymethyl cellulose: 16.8 mg/tablet
Talc powder: 4.2 mg/tablet
Sodium stearyl fumarate: 12.0 mg/tablet
Total: 405 mg/tablet
Preparation procedures of the tablets are the same as those of example 62.

Example 64 Preparation of Coated Tablets

The tablets (plain tablets) prepared in example 62 were coated using a high-efficiency coating machine with the coating powders (based on each tablet) consisting of 2.0 mg of iron oxide yellow, 5.0 mg of polyethylene glycol, 1.5 mg of talc powder and 1.5 mg of titanium dioxide. The tablets (plain tablets) prepared in example 63 were coated using a high-efficiency coating machine with the coating powder (based on each tablet) consisting of 4.0 mg of iron oxide yellow, 11.0 mg of polyethylene glycol, 2.5 mg of talc powder and 2.5 mg of titanium dioxide.

Example 65 Preparation of Capsules

Capsules were prepared with canagliflozin Monohydrate Form HI or canagliflozin Monohydrate Form HII of the present invention as the active pharmaceutical ingredient, and each capsule contained 100 mg of canagliflozin. The formula of capsules was as follows:
Canagliflozin Monohydrate Form HI or canagliflozin Monohydrate Form HII of the present invention: 104.0 mg/capsule
Lactose: 45.6 mg/capsule
Corn starch: 12.4 mg/capsule
Polyvidone: 13.0 mg/capsule
Total: 175.0 mg/capsule
Preparation Procedures of the Capsules (Scale: 10000 Capsules) were as Follows:
1) Dissolve polyvidone in water to form a solution.
2) Pass canagliflozin Monohydrate Form HI or canagliflozin Monohydrate Form HII of the present invention through a 100-mesh sieve, then mix well with lactose and corn starch, add the polyvidone solution to the mixed powders to prepare a soft material, and pass the soft material through a sieve with 20 to 40 meshes for granulation, and dry.
Fill the dried granules in capsule shells. A total of 10,000 capsules were made.

Example 66 Preparation of Capsules

Capsules were prepared with canagliflozin Monohydrate Form HI or canagliflozin Monohydrate Form HII of the present invention as the active pharmaceutical ingredient, and each capsule contained 300 mg of canagliflozin. The formula of capsules was as follows:
Canagliflozin Monohydrate Form HI or canagliflozin Monohydrate Form HII of the present invention: 312.0 mg/capsule
Lactose: 136.8 mg/capsule
Corn starch: 37.2 mg/capsule
Polyvidone: 39.0 mg/capsule
Total: 525.0 mg/capsule
Preparation procedures of the capsules were the same as those of example 65.

Example 67 Preparation of Suspension

An oral suspension was prepared with canagliflozin Monohydrate Form HI or canagliflozin Monohydrate Form HII of the present invention as the active pharmaceutical ingredient. The strength is 50 mL/vial and each vial contains 104 mg of canagliflozin Monohydrate Form HI or canagliflozin Monohydrate Form HII (equivalent to 100 mg of canagliflozin).
The Formula of the Oral Suspension was as Follows:
Canagliflozin Monohydrate Form HI or canagliflozin Monohydrate Form HII of the present invention: 2.08 g (equivalent to 2 g of canagliflozin)
Xanthan gum: 8 g
Sodium dihydrogen citrate: 2 g
Methyl p-hydroxybenzoate: 1.4 g
Simple syrup: 150 mL
Orange essence: 1 mL
Water: q.s. to 1000 mL
Preparation Procedures of the Oral Suspension were as Follows:
Mix canagliflozin Monohydrate Form HI or canagliflozin Monohydrate Form HII of the present invention, xanthan gum, sodium dihydrogen citrate, methyl p-hydroxybenzoate, and simple syrup with orange essence, add water to 1000 mL, and shake for dispersing into a suspension, aliquot to prepare 20 vials.

Comparative Example 1

The competitive stability test of canagliflozin Monohydrate Form HI of the present invention, the known canagliflozin, canagliflozin hemihydrate Form hH1 and canagliflozin Form A was performed in water at room temperature.
Conditions of the competitive stability test were as follows: take equal quantity (250 mg) samples of canagliflozin Monohydrate Form HI of the present invention, canagliflozin prepared in the preparation example 1, canagliflozin Form A prepared in the preparation example 2 and canagliflozin hemihydrate Form hH1 prepared in the preparation example 3 respectively, mix the samples with 5 mL of water to form a suspension. The suspension was stirred for 7 days at room temperature and then XRPD characterization analysis was performed.
The XRPD pattern of the suspension after 7 days showed that the crystalline form was canagliflozin Monohydrate Form HI. Therefore, by the competitive stability test in water at room temperature, the known canagliflozin, canagliflozin hemihydrate Form hH1 and canagliflozin Form A all transformed to canagliflozin Monohydrate Form HI of the present invention, while canagliflozin Monohydrate Form HI of the present invention maintained its original crystalline form.
The result of the competitive stability test indicated that canagliflozin Monohydrate Form HI of the present invention was more stable than the known canagliflozin, canagliflozin hemihydrate Form hH1 and canagliflozin Form A in water or aqueous system.

Comparative Example 2

The competitive stability test among canagliflozin Monohydrate Form HII of the present invention, the known Canagliflozin, canagliflozin hemihydrate Form hH1 and canagliflozin Form A was performed in water at room temperature.

Conditions of the competitive stability test were as follows: take equal quantity (250 mg) samples of canagliflozin Monohydrate Form HII of the present invention, canagliflozin prepared in the preparation example 1 in the present invention, canagliflozin Form A prepared in the preparation example 2 in the present invention and canagliflozin hemihydrate Form hH1 prepared in the preparation 3 in the present invention, respectively, and mix the samples with 3 mL of water to form a suspension. The suspension was stirred for 7 days at room temperature and then XRPD characterization analysis was performed.

The XRPD pattern of the suspension after 7 days showed that the crystalline form was canagliflozin Monohydrate Form HII. Therefore, the competitive stability test in water at room temperature demonstrates the known canagliflozin, canagliflozin hemihydrate Form hH1 and canagliflozin Form A all transformed to canagliflozin Monohydrate Form HII of the present invention, while canagliflozin Monohydrate Form HII of the present invention maintained its original crystalline form.

The result of the competitive stability test indicated that canagliflozin Monohydrate Form HII of the present invention was more stable than the known canagliflozin, canagliflozin hemihydrate Form hH1 and canagliflozin Form A in water or aqueous system.

All patent documents quoted in the specifications are incorporated by reference in their entireties.

The general descriptions of the invention and the descriptions of its embodiments in the present invention should not be understood as limits to the technical scheme of the present invention.

What is claimed is:

1. Canagliflozin Monohydrate represented by the following structural formula:

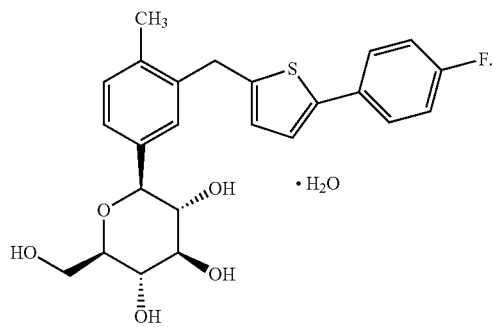 [SMILES: Cc1ccc([C@@H]2O[C@H](CO)[C@@H](O)[C@H](O)[C@H]2O)cc1Cc1ccc(-c2ccc(F)cc2)s1 ; "· H2O"]

2. A pharmaceutical composition comprising a therapeutically effective amount of canagliflozin Monohydrate according to claim 1, and at least one pharmaceutically acceptable carrier selected from the group consisting of diluents, adhesives, disintegrants, lubricants, glidants, complex forming agents, and release rate controllers.

3. The pharmaceutical composition according to claim 2, wherein the pharmaceutical composition is in a dosage form selected from the group consisting of tablets, capsules, granules, pulvis, pills, powder, solutions, syrups, suspensions and emulsions for oral administration, or intravenous infusion or injections for parenteral administration.

4. A method of treating the diseases selected from the group consisting of diabetes, diabetic retinopathy, diabetic neuropathy, diabetic nephropathy, postprandial hyperglycemia, delayed wound healing, insulin resistance, hyperglycemia, hyperinsulinemia, elevated blood levels of fatty acids, elevated blood levels of glycerol, hyperlipidemia, adiposity, hypertriglyceridemia, syndrome X, atherosclerosis and hypertension, which comprises administering to an elderly patient in need, a therapeutically effective amount of canagliflozin Monohydrate according to claim 1, in an oral suspension.

5. A method of treating the diseases selected from the group consisting of diabetes, diabetic retinopathy, diabetic neuropathy, diabetic nephropathy, postprandial hyperglycemia, delayed wound healing, insulin resistance, hyperglycemia, hyperinsulinemia, elevated blood levels of fatty acids, elevated blood levels of glycerol, hyperlipidemia, adiposity, hypertriglyceridemia, syndrome X, atherosclerosis and hypertension, which comprises administering to a patient in need, a therapeutically effective amount of the pharmaceutical composition according to claim 2.

6. A method of treating the diseases selected from the group consisting of diabetes, diabetic retinopathy, diabetic neuropathy, diabetic nephropathy, postprandial hyperglycemia, delayed wound healing, insulin resistance, hyperglycemia, hyperinsulinemia, elevated blood levels of fatty acids, elevated blood levels of glycerol, hyperlipidemia, adiposity, hypertriglyceridemia, syndrome X, atherosclerosis and hypertension, which comprises administering to a patient in need, a therapeutically effective amount of the pharmaceutical composition according to claim 3.

* * * * *